(12) United States Patent
Hoffman et al.

(10) Patent No.: US 10,660,544 B2
(45) Date of Patent: *May 26, 2020

(54) SELF-COMPENSATING BED SCALE SYSTEM FOR REMOVABLE COMPONENTS

(71) Applicant: HILL-ROM SERVICES, INC., Batesville, IN (US)

(72) Inventors: Brian J. Hoffman, Lawrenceburg, IN (US); Mike J. Viltro, Hamilton, OH (US); Chris L. Hildenbrand, Greensburg, IN (US); James L. Walke, Batesville, IN (US); Aziz A. Bhai, Fishers, IN (US); Eric R. Meyer, Batesville, IN (US); David C. Newkirk, Lawrenceburg, IN (US); Frank Sauser, Cincinnati, OH (US); Nicole Johannigman, Greensburg, IN (US); Brandon P. Fisk, Greensburg, IN (US)

(73) Assignee: Hill-Rom Services, Inc., Batesville, IN (US)

(*) Notice: Subject to any disclaimer, the term of this patent is extended or adjusted under 35 U.S.C. 154(b) by 4 days.

This patent is subject to a terminal disclaimer.

(21) Appl. No.: 16/046,046

(22) Filed: Jul. 26, 2018

(65) Prior Publication Data
US 2018/0333082 A1    Nov. 22, 2018

Related U.S. Application Data

(63) Continuation of application No. 15/137,306, filed on Apr. 25, 2016, now Pat. No. 10,045,715.
(Continued)

(51) Int. Cl.
A61B 5/11 (2006.01)
A61G 7/05 (2006.01)
(Continued)

(52) U.S. Cl.
CPC .......... A61B 5/1115 (2013.01); A61B 5/6892 (2013.01); A61B 5/7278 (2013.01);
(Continued)

(58) Field of Classification Search
CPC ..... A61B 5/115; A61B 5/6892; A61B 5/7278; A61B 5/742; A61B 5/7475;
(Continued)

(56) References Cited

U.S. PATENT DOCUMENTS 3,217,818 A    11/1965    Engelsher et al.
3,876,018 A    4/1975    Mracek et al.
(Continued)

FOREIGN PATENT DOCUMENTS

EP    1975750 A2    10/2008

OTHER PUBLICATIONS

Search Report for Related European Application 16167021.1-1651, 7 pages.
(Continued)

Primary Examiner — Randy W Gibson
(74) Attorney, Agent, or Firm — Barnes & Thornburg LLP

(57) ABSTRACT

A patient support apparatus includes detectors and a controller operable to automatically update a tare weight for use in determining a true patient weight. The detectors are configured to produce signals indicating a presence or absence of a corresponding removable component. The controller is configured to determine weights of each and every removable component on the patient support apparatus and store each weight in a memory. The controller is further configured to receive the signals produced by the detectors and detect any addition or removal of removable components of the patient support apparatus, update the tare
(Continued)

weight, and determine a weight of a patient being supported on the patient support apparatus.

20 Claims, 16 Drawing Sheets

Related U.S. Application Data

(60) Provisional application No. 62/153,128, filed on Apr. 27, 2015.

(51) Int. Cl.
*G01G 19/44* (2006.01)
*G01G 19/52* (2006.01)
*G01G 23/14* (2006.01)
*A61B 5/00* (2006.01)
*A61G 9/00* (2006.01)
*A61G 7/002* (2006.01)
*A61G 7/018* (2006.01)

(52) U.S. Cl.
CPC ............ *A61B 5/742* (2013.01); *A61B 5/7475* (2013.01); *A61G 7/002* (2013.01); *A61G 7/018* (2013.01); *A61G 7/05* (2013.01); *A61G 7/0506* (2013.01); *A61G 7/0507* (2013.01); *A61G 7/0527* (2016.11); *A61G 9/006* (2013.01); *G01G 19/44* (2013.01); *G01G 19/52* (2013.01); *G01G 23/14* (2013.01); *A61B 2562/0252* (2013.01); *A61G 2203/44* (2013.01); *A61M 2209/08* (2013.01)

(58) Field of Classification Search
CPC .......... A61B 2562/0252; A61G 7/0527; A61G 7/002; A61G 7/018; A61G 7/05; A61G 7/0506; A61G 7/0507; A61G 9/006; A61G 2203/44; G01G 19/44; G01G 19/445; G01G 19/52; G01G 23/14; A61M 2209/08
See application file for complete search history.

(56) References Cited

U.S. PATENT DOCUMENTS

| | | | |
|---|---|---|---|
| 4,015,677 A | 4/1977 | Silva et al. | |
| 4,023,633 A | 5/1977 | Swersey et al. | |
| 4,363,368 A | 12/1982 | Paddon et al. | |
| 4,551,882 A | 11/1985 | Swersey et al. | |
| 4,601,356 A | 7/1986 | Muccillo | |
| 4,751,754 A | 6/1988 | Bailey et al. | |
| 4,953,244 A | 9/1990 | Koerber et al. | |
| 5,131,103 A | 7/1992 | Thomas et al. | |
| 5,245,718 A | 9/1993 | Krauska | |
| 5,276,432 A * | 1/1994 | Travis | A61B 5/1115 177/144 |
| 5,393,938 A * | 2/1995 | Bumbalough | G01G 19/445 177/144 |
| 5,808,552 A | 9/1998 | Wiley et al. | |
| 5,823,278 A * | 10/1998 | Geringer | G01G 19/52 177/144 |
| 5,831,221 A | 11/1998 | Geringer et al. | |
| 5,859,390 A | 1/1999 | Stafford et al. | |
| 5,861,582 A | 1/1999 | Flanagan et al. | |
| 5,906,016 A | 5/1999 | Ferrand et al. | |
| 6,067,019 A | 5/2000 | Scott | |
| 6,092,838 A | 7/2000 | Walker | |
| 6,133,837 A | 10/2000 | Riley | |
| 6,208,250 B1 | 3/2001 | Dixon et al. | |
| 6,320,510 B2 | 11/2001 | Menkedick et al. | |
| 6,438,776 B2 | 8/2002 | Ferrand et al. | |
| 6,469,263 B1 | 10/2002 | Johnson | |
| 6,481,688 B1 | 11/2002 | Welling et al. | |
| 6,560,798 B2 | 5/2003 | Welling et al. | |
| 6,668,408 B2 | 12/2003 | Ferrand et al. | |
| 6,680,443 B2 | 1/2004 | Dixon | |
| 6,761,344 B2 | 7/2004 | Welling et al. | |
| 6,791,460 B2 | 9/2004 | Dixon et al. | |
| 6,793,279 B2 | 9/2004 | Hoffman et al. | |
| 6,829,796 B2 | 12/2004 | Salvatini et al. | |
| 6,907,630 B2 | 6/2005 | Treon | |
| 6,924,441 B1 | 8/2005 | Mobley et al. | |
| 7,176,391 B2 | 2/2007 | Metz et al. | |
| 7,281,284 B2 | 10/2007 | Sims, Jr. | |
| 7,310,839 B2 | 12/2007 | Salvatini et al. | |
| 7,335,839 B2 | 2/2008 | Metz et al. | |
| 7,459,645 B2 | 12/2008 | Skinner et al. | |
| 7,469,436 B2 | 12/2008 | Meyer et al. | |
| 7,478,446 B2 | 1/2009 | Sims, Jr. | |
| 7,557,718 B2 | 7/2009 | Petrosenko et al. | |
| 7,600,434 B2 | 10/2009 | Bak | |
| 7,681,260 B2 | 3/2010 | Hallock et al. | |
| 7,698,765 B2 | 4/2010 | Bobey et al. | |
| 7,714,238 B2 | 5/2010 | Skinner et al. | |
| 7,818,831 B2 | 10/2010 | Mahdjoubi | |
| 7,834,768 B2 | 11/2010 | Dixon et al. | |
| 7,937,791 B2 | 5/2011 | Meyer et al. | |
| 7,973,666 B2 | 7/2011 | Petrosenko et al. | |
| 7,978,084 B2 | 7/2011 | Dixon et al. | |
| 7,986,242 B2 | 7/2011 | Dixon et al. | |
| 8,056,950 B2 | 11/2011 | Souke et al. | |
| 8,112,836 B2 | 2/2012 | Tesar et al. | |
| 8,146,191 B2 | 4/2012 | Bobey et al. | |
| 8,196,240 B2 | 6/2012 | Meyer et al. | |
| 8,258,963 B2 | 9/2012 | Dixon et al. | |
| 8,261,381 B2 | 9/2012 | Hallock et al. | |
| 8,266,743 B2 | 9/2012 | Jones et al. | |
| 8,344,860 B2 | 1/2013 | Collins, Jr. et al. | |
| 8,400,311 B2 | 3/2013 | Dixon et al. | |
| 8,432,287 B2 | 4/2013 | O'Keefe et al. | |
| 8,464,380 B2 | 6/2013 | Bobey et al. | |
| 8,525,682 B2 | 9/2013 | Dixon et al. | |
| 8,537,008 B2 | 9/2013 | Tallent et al. | |
| 8,593,284 B2 | 11/2013 | Tallent et al. | |
| 8,598,893 B2 | 12/2013 | Camus | |
| 8,717,181 B2 | 5/2014 | Tallent et al. | |
| 8,745,788 B2 | 6/2014 | Bhai | |
| 8,830,070 B2 | 9/2014 | Dixon et al. | |
| 8,844,079 B2 | 9/2014 | Skinner et al. | |
| 8,847,756 B2 | 9/2014 | Tallent et al. | |
| 8,921,717 B2 | 12/2014 | Siegel et al. | |
| 8,959,680 B2 | 2/2015 | Tesar et al. | |
| 8,973,186 B2 | 3/2015 | Bhai | |
| 9,220,650 B2 | 12/2015 | Bobey et al. | |
| 10,045,715 B2 | 8/2018 | Hoffman et al. | |
| 2003/0010345 A1 | 1/2003 | Koblasz et al. | |
| 2005/0035871 A1 | 2/2005 | Dixon et al. | |
| 2005/0077861 A1 | 4/2005 | Treon | |
| 2005/0091753 A1 | 5/2005 | Salvatini et al. | |
| 2005/0166324 A1 | 8/2005 | Dixon et al. | |
| 2005/0273940 A1 | 12/2005 | Petrosenko et al. | |
| 2006/0059814 A1 | 3/2006 | Metz et al. | |
| 2006/0195986 A1 | 9/2006 | Hakamiun et al. | |
| 2007/0094792 A1 | 5/2007 | Sims | |
| 2007/0107948 A1 | 5/2007 | Metz et al. | |
| 2007/0268147 A1 | 11/2007 | Bhai | |
| 2007/0272450 A1 | 11/2007 | Skinner et al. | |
| 2008/0010747 A1 | 1/2008 | Dixon et al. | |
| 2008/0066230 A1 | 3/2008 | Hallock et al. | |
| 2009/0013462 A1 | 1/2009 | Mahdjoubi | |
| 2009/0084609 A1 | 4/2009 | Skinner et al. | |
| 2009/0139032 A1 | 6/2009 | Bak | |
| 2009/0217460 A1 | 9/2009 | Bobey et al. | |
| 2009/0270770 A1 | 10/2009 | Petrosenko et al. | |
| 2010/0308846 A1 | 12/2010 | Camus | |
| 2011/0010858 A1 | 1/2011 | Tesar et al. | |
| 2011/0037597 A1 | 2/2011 | Dixon et al. | |
| 2011/0094031 A1 | 4/2011 | Tesar et al. | |
| 2014/0080413 A1* | 3/2014 | Hayes | H04B 5/0037 455/41.1 |
| 2014/0124273 A1 | 5/2014 | Receveur et al. | |

(56) References Cited

U.S. PATENT DOCUMENTS

2014/0151577 A1    6/2014  Kreschollek et al.
2016/0022218 A1*  1/2016  Hayes .................... A61G 7/005
                                                               600/301
2016/0310045 A1   10/2016  Hoffman et al.

OTHER PUBLICATIONS

Bib Data Sheet for WO 2014/151577 from the EPO website; Dec. 15, 2017.
Detailed Description section from WO 2014/151577, from the EPO website; Dec. 15, 2017.

* cited by examiner

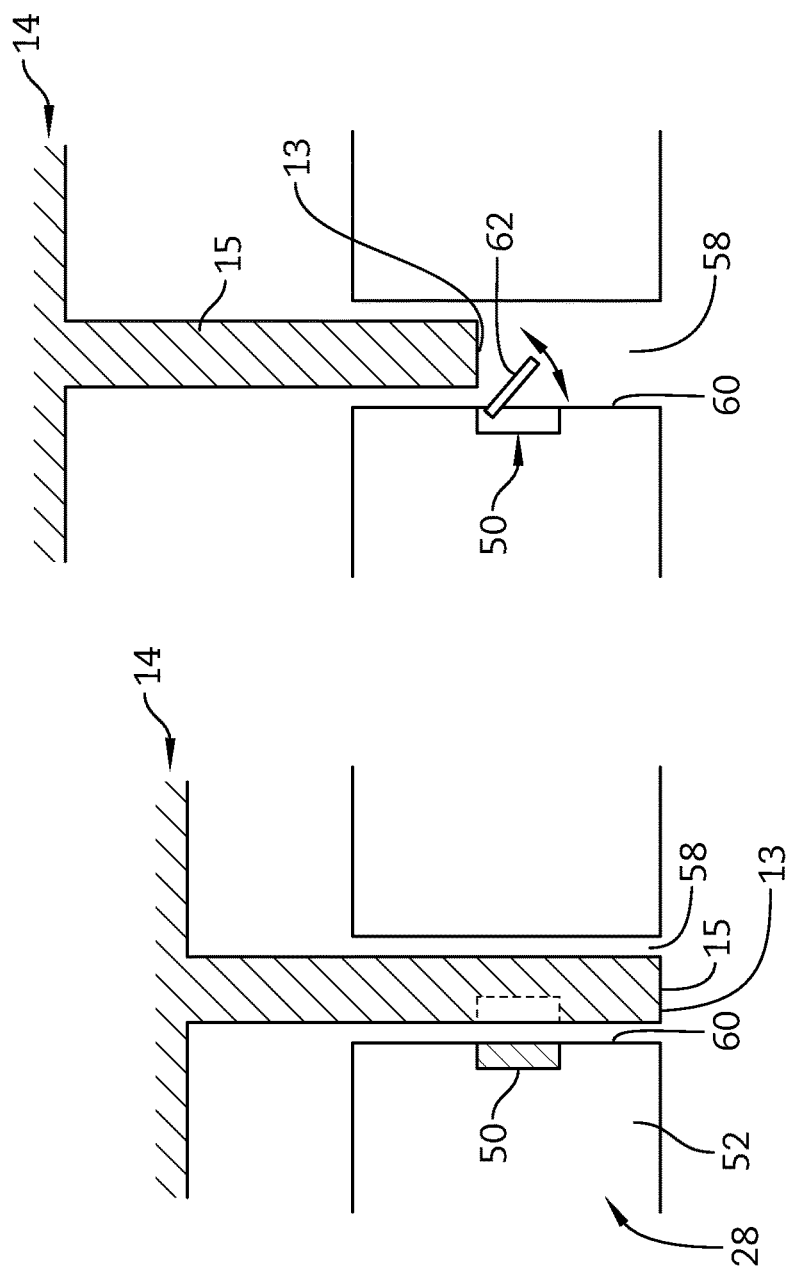

SELF-COMPENSATING BED SCALE SYSTEM FOR REMOVABLE COMPONENTS

CROSS-REFERENCE TO RELATED APPLICATIONS

The present application is a continuation of U.S. application Ser. No. 15/137,306, entitled "SELF-COMPENSATING BED SCALE SYSTEM FOR REMOVABLE COMPONENTS," which was filed on Apr. 25, 2016, which claims priority under 35 U.S.C. § 119(e) to U.S. Provisional Application No. 62/153,128, which was filed Apr. 27, 2015, each of which is hereby incorporated by reference.

BACKGROUND

The present disclosure is related to a patient support apparatus that includes a control system for automatically calculating a true weight of a patient placed on the patient support apparatus. More specifically, the present disclosure is directed to a patient support apparatus having removable components such as headboard, footboard, siderail, infusion support, drainage container, or urinal container.

In a care facility, such as a hospital or a nursing home, patients are often placed on patient support apparatuses for an extended period of time. Patients who are positioned on the patient support apparatus for extended periods have an increased risk of developing certain complications or injuries, such as certain skin condition that may increase the potential of nosocomial pressure ulcers occurring. In an effort to mitigate or prevent such complications or injuries, some patient support apparatuses use load information gathered from an integrated scale system to derive pressure set points for a dynamic support surface, which continually redistributes the pressure of the dynamic support surface against the patient's skin. However, the weight attributable to the added or removed removable components while the patient remains on a patient support apparatus often causes errors in calculating the true weight of the patient, which in turn can lead to non-optimal pressure set points being derived from dynamic support surfaces.

In addition, caregivers often monitor the weight of a patient who is in a care facility to diagnose and treat certain medical conditions. For example, some caregivers closely monitor a patient's weight loss or weight gain throughout a course of treatment to determine, for example, whether the patient is retaining water. To facilitate making those determinations, some caregivers use an amount of weight calculated by the patient support apparatus upon which the patient is being supported. The weight attributable to added or removed removable components while the patient remains on the patient support apparatus may cause incorrect weight readings and result in incorrect diagnosis or treatment to certain medical conditions.

SUMMARY

The present application discloses one or more of the features recited in the appended claims and/or the following features which, alone or in any combination, may comprise patentable subject matter:

According to a first aspect of the present disclosure, a patient support apparatus comprises a patient support, a plurality of load cells, a plurality of detectors, and a controller. The plurality of load cells supports the patient support. Each load cell is configured to produce a signal indicative of an amount of weight on that load cell. Each detector is configured to produce a signal indicative of a presence of a corresponding removable component. The controller is in communication with the plurality of the load cells and the plurality of detectors. The controller is configured to receive the signal produced by each of the load cells and the detectors. The controller is also configured to determine a weight of the patient being supported on the patient support. The controller is further configured to detect, subsequent to determining the weight of the patient, any subsequent removal or addition of one or more of the removable components of the patient support apparatus based on the signals produced by the plurality of detectors. The controller is still yet configured to update the weight of the patient being supported on the patient support considering the effect of the removal or addition of the one or more of the removable components.

In some embodiments, the controller may be further configured to determine an initial tare weight of the empty patient support apparatus, and determine whether the patient support is supporting a patient as a function of the signals produced by the plurality of load cells.

In some embodiments, the controller may be further configured to determine whether the patient support is supporting the patient by determining a current occupancy state of the patient support apparatus. The current occupancy state of the patient support apparatus may comprise at least one of an occupied state and an unoccupied state. The occupied state may be indicated when the patient support is determined to be supporting the patient and the unoccupied state may be indicated when the patient support is determined not to be supporting the patient.

In some embodiments, the controller is further configured to the controller may be further configured to automatically update the tare weight of the patient support apparatus.

In some embodiments, the tare weight of the patient support apparatus may include the total amount of weight of the empty patient support apparatus being compensated for a first amount of weight and second amount of weight, the first amount of weight corresponding to the weight of the subsequently added removable components, and the second amount of weight corresponding to the weight of the subsequently removed removable components of the patient support apparatus.

In some embodiments, updating the tare weight in response to detecting the addition or removal of the removable components may include updating the tare weight in response to (i) determining that the patient support is no longer supporting the patient, (ii) storing the removable components initially detected on the empty patient support apparatus, (iii) storing total weight of the empty patient support apparatus as a function of initial tare weight, and (iv) updating the tare weight by supplementing the weight of the removable components added to the patient support apparatus or by offsetting the weight of the removable components removed from the patient support apparatus in response to signals received from the plurality of detectors.

In some embodiments, the controller may be further configured to determine a normalized amount of weight of each removable component of the patient support apparatus as a function of the signals produced by the plurality of load cells. The controller may be still further configured to detect the removable components currently attached to the patient support apparatus in response to detecting a presence or absence of the corresponding removable component by the plurality of detectors. Yet further, the controller may be configured to determine and store a total weight of the removable components currently attached to the patient support apparatus. The controller may be still further configured to detect any subsequent addition or removal of the removable components from the patient support apparatus.

In some embodiments the controller may be further configured to set an initial occupancy state of the patient support apparatus to an unoccupied state. The controller may determine a normalized amount of weight on the plurality of load cells as a function of the signals produced by the plurality of load cells. The controller may also set the current occupancy state of the patient support apparatus to the occupied state in response to the normalized amount of weight on the plurality of load cells satisfying an occupied condition, the occupied condition defining a first normalized threshold value for which the normalized amount of weight on the plurality of load cells must exceed. The controller may still yet be configured to set the current occupancy state of the patient support apparatus to the unoccupied state in response to the normalized amount of weight on the plurality of load cells satisfying an unoccupied condition, the unoccupied condition defining a second normalized threshold value for which the normalized amount of weight on the plurality of load cells must be below.

In some embodiments, the controller is further configured to determine, in response to determining that the patient support is no longer supporting the patient, a total amount of weight of the empty patient support apparatus as a function of signals received from the plurality of load cells. The controller may also be configured to set and store the total amount of weight of the empty patient support apparatus as an initial tare weight of the patient support apparatus.

In some embodiments, the total amount of weight of the empty patient support apparatus may include the amount of weight on the plurality of load cells of the empty patient support apparatus. The amount of weight of the empty patient support apparatus may also include the total amount of weight of the removable components currently attached to the empty patient support apparatus.

In some embodiments, updating a weight of the patient may include (i) determining the empty patient support apparatus as a function of signals received from the plurality of load cells, (ii) determining the presence or absence of removable components of the patient support apparatus in response to the signals received from the plurality of detectors, (iii) determining the tare weight of the patient support apparatus, and (iv) offsetting the updated tare weight from the total amount of weight of the patient support apparatus.

In some embodiments, the controller may comprise a processor; and at least one machine-readable storage medium including a plurality of instructions. The instructions may, in response to being executed by the processor, automatically determine the patient weight based on the signals from the load cells and the sensors.

In some embodiments, determining the presence or absence of removable components of the patient support apparatus may include detecting the signal produced by one or more corresponding detectors associated with each removable component.

In some embodiments, the removable component of the patient support apparatus may include a headboard, a footboard, a siderail, an infusion support, a drainage container, or a urinal container.

In some embodiments, the patient support apparatus may further include a user interface that includes a graphical display and the presence or absence of any one of the removable components may be indicated by an icon representation of the patient support apparatus.

In some embodiments, the information regarding the presence or absence of removable components may be transmitted to a graphical display remote from the patient support apparatus.

In some embodiments, the remote graphical display may be a mobile computing device associated with a particular caregiver.

According to a second aspect of the present disclosure, a method of determining and displaying a patient weight on a patient support apparatus includes receiving information from a plurality of load cells configured to support the patient, each load cell configured to produce a signal indicative of an amount of weight on that load cell. The method also includes receiving information from a plurality of detectors, each detector configured to produce a signal indicative of a presence of a corresponding removable component of the patient support apparatus. The method further includes determining, from the information, a weight of the patient being supported on the patient support. The method also includes detecting, subsequent to determining the weight of the patient, any subsequent removal or addition of one or more of the removable components of the patient support apparatus based on the signals produced by the plurality of detectors. The method still further includes updating the weight of the patient being supported on the patient support considering the effect of the removal or addition of the one or more of the removable components.

In embodiments, the method may further include determining an initial tare weight of the empty patient support apparatus and determining whether the patient support is supporting a patient as a function of the signals produced by the plurality of load cells.

In embodiments, the method may further include determining whether the patient support is supporting the patient comprises determining a current occupancy state of the patient support apparatus, wherein the current occupancy state of the patient support apparatus comprises at least one of an occupied state and an unoccupied state, the occupied state being indicated when the patient support is determined to be supporting the patient and the unoccupied state being indicated when the patient support is determined not to be supporting the patient.

In embodiments, the method may further include automatically updating the tare weight of the patient support apparatus.

In embodiments, the tare weight of the patient support apparatus may include the total amount of weight of the empty patient support apparatus being compensated for a first amount of weight and second amount of weight, the first amount of weight corresponding to the weight of the subsequently added removable components, and the second amount of weight corresponding to the weight of the subsequently removed removable components of the patient support apparatus.

In embodiments, the method may further include updating a tare weight in response to detecting the addition or removal of the removable components comprises updating the tare weight in response to (i) determining that the patient support is no longer supporting the patient, (ii) storing the removable components initially detected on the empty patient support apparatus, (iii) storing total weight of the empty patient support apparatus as a function of initial tare weight, and (iv) updating the tare weight by supplementing the weight of the removable components added to the patient support apparatus or by offsetting the weight of the removable components removed from the patient support apparatus in response to signals received from the plurality of detectors.

In embodiments, the method may further include determining a normalized amount of weight of each removable component of the patient support apparatus as a function of the signals produced by the plurality of load cells, detecting the removable components currently attached to the patient support apparatus in response to detecting a presence or absence of the corresponding removable component by the plurality of detectors, determining and storing a total weight of the removable components currently attached to the patient support apparatus, and detecting any subsequent addition or removal of the removable components from the patient support apparatus.

In embodiments, the method may further include determining the presence or absence of removable components of the patient support apparatus comprises detecting the signal produced by one or more corresponding detectors associated with each removable component.

In embodiments, a removable component of the patient support apparatus may include a headboard, footboard, siderail, infusion support, drainage container, or a urinal container.

In embodiments, the method may further include graphically indicating the presence or absence of any one of the removable components by an icon representation of the patient support apparatus.

According to a third aspect of the present disclosure, a method of determining the weight of one or more removable components of a patient support apparatus that includes a plurality of load cells comprises determining an initial tare weight for the patient support apparatus. The method further includes prompting a user to add a first removable component to the patient support apparatus. The method further includes detecting the presence of the removable component by a sensor associated with the removable component. The method still further includes determining, using the load cells, the weight of the removable component.

In embodiments, the method may further include storing the weight of the first removable component in a memory device.

In embodiments, the method may further include determining an updated tare weight based on the added weight of the first removable component.

In embodiments, the method may further include storing the updated tare weight in a memory device.

In embodiments, the method may further include prompting a user to add a second removable component to the patient support apparatus, detecting the presence of the second removable component based on a signal associated with the second removable component, and determining, using the load cells, the weight of the second removable component.

In embodiments, the method may further include storing the weight of the second removable component in a memory device.

In embodiments, the method may further include determining an updated tare weight based on the added weight of the second removable component.

In embodiments, the method may further include storing the updated tare weight in a memory device.

In embodiments, the method may further include monitoring the sensor associated with the first removable component and the sensor associated with the second removable component to determine if either the first or second removable component is removed, and, if a removable component is detected to be removed, updating the tare weight to account for the removal of the weight of the component that has been removed.

According to a fourth aspect of the present disclosure, a patient support apparatus includes a patient support, a plurality of load cells, a plurality of detectors, and a controller. The plurality of load cells supports the patient support. Each load cell is configured to produce a signal indicative of an amount of weight on that load cell. Each detector is configured to produce a signal indicative of a presence of a corresponding removable component. The controller is in communication with the plurality of load cells and the plurality of detectors. The controller is configured to receive the signal produced by each of the plurality of load cells and each of the plurality of detectors, determine an initial tare weight of the empty patient support apparatus, determine whether the patient support is supporting a patient as a function of the signals produced by the plurality of load cells, and determine the weight of the patient being supported on the patient support. The controller is further configured to detect, subsequent to determining the weight of the patient, any subsequent removal or addition of the removable components of the patient support apparatus, update the tare weight of the patient support apparatus, and update the weight of the patient being supported on the patient support.

In some embodiments, the controller is configured to determine the normalized amount of weight of each removable component of the patient support apparatus as a function of the signals produced by the plurality of load cells. The controller is further configured to detect the removable component currently attached to the patient support apparatus in response to detecting a presence or absence of the corresponding removable component by the plurality of detectors, determine and store the total weight of the removable components currently attached to the patient support apparatus, and detect any subsequent removal or addition of the removable components on the patient support apparatus.

In some embodiments, determining whether the patient support is supporting the patient may further include determining a current occupancy state of the patient support apparatus.

In some embodiments, the current occupancy state of the patient support apparatus may further include at least one of an occupied state and an unoccupied state. The occupied state is indicated when the patient support is determined to be supporting the patient and the unoccupied state is indicated when the patient support is determined not to be supporting the patient.

In some embodiments, the controller is further configured to set an initial occupancy state of the patient support apparatus to the unoccupied state and determine a normalized amount of weight on the plurality of load cells as a function of the signals produced by the plurality of load cells. The controller is further configured to set the current occupancy state of the patient support apparatus to the occupied state in response to the normalized amount of weight on the plurality of load cells satisfying an occupied condition. The occupied condition defines a first normalized threshold value for which the normalized amount of weight on the plurality of load cells must exceed. The controller may further be configured to set the current occupancy state of the patient support apparatus to the unoccupied state in response to the normalized amount of weight on the plurality of load cells satisfying an unoccupied condition. The unoccupied condition defines a second normalized threshold value for which the normalized amount of weight on the plurality of load cells must be below.

In some embodiments, the controller is further configured to determine, in response to determining that the patient support is no longer supporting the patient, a total amount of weight of the empty patient support apparatus as a function of signals received from the plurality of load cells, and set and store the total amount of weight of the empty patient support apparatus as an initial tare weight of the patient support apparatus.

In some embodiments, the total amount of weight of the empty patient support apparatus comprises the amount of weight on the plurality of load cells of the non-patient support apparatus. The amount of weight of the non-patient support apparatus may further include the total amount of weight of the removable components currently attached to the patient support apparatus.

In some embodiments, the tare weight of the patient support apparatus comprises the total amount of weight of the empty patient support apparatus being compensated for a first amount of weight and second amount of weight. The first amount of weight corresponds to the weight of the subsequently added removable component and the second amount of weight corresponds to the weight of the subsequently removed removable components of the patient support apparatus.

In some embodiments, updating the tare weight of the patient support apparatus in response to detecting the addition or removal of the removable components comprises updating the tare weight in response to (i) determining that the patient support is no longer supporting the patient, (ii) storing the removable components initially detected on the empty patient support apparatus, (ii) storing total weight of the empty patient support apparatus as a function of initial tare weight, and (iv) updating the tare weight by supplementing the weight of the removable components added to the patient support apparatus or by offsetting the weight of the removable components removed from the patient support apparatus in response to signals received from the plurality of detectors.

In some embodiments, updating a weight of the patient may further include (i) determining the empty patient support apparatus as a function of signals received from the plurality of load cells, (ii) determining the presence or absence of removable components of the patient support apparatus based on signals received from the plurality of detectors, (iii) determining the updated tare weight of the patient support apparatus, and (iv) offsetting the updated tare weight from the total weight of the patient support apparatus.

In a fifth aspect of the present disclosure, a patient support apparatus includes a processor and at least one machine-readable storage medium. The at least one machine-readable storage medium includes a plurality of instructions, that in response to being executed by the processor, result in the patient support apparatus receiving, (i) a signal produced by each of a plurality of load cells supporting a patient support of the patient support apparatus, the signal produced by each load cell indicating an amount of weight on that load cell, and (ii) a signal produced by each of the plurality of detectors associated with each removable components of the patient support apparatus, the signal produced by each detector indicating the presence or absence of the removable component. The at least one machine-readable storage medium further includes a plurality of instructions, that in response to being executed by the processor, result in the patient support apparatus determining a tare weight of the patient support apparatus by compensating the weight indicated by the load cells, determining a weight of a patient being supported on the patient support by offsetting the tare weight from the weight indicated by the load cells, detecting, subsequent to determining the weight of the patient, further changes in the tare weight of the patient support apparatus, and updating the weight of the patient by updating the tare weight of the patient support apparatus.

In some embodiments, determining the presence or absence of removable components of the patient support apparatus comprises detecting the signal produced by one or more corresponding detectors associated with each removable component.

In some embodiments, the removable component of the patient support apparatus may further include headboard, footboard, siderail, infusion support, drainage container, or urinal container.

In some embodiments, the tare weight of the patient support apparatus comprises a current weight of the empty patient support apparatus including a current weight of the removable components that are detected.

In some embodiments, each load cell is configured to produce a signal indicative of an amount of weight on that load cell and the plurality of load cells is configured to produce a signal indicative of a total amount of weight on the patient support apparatus.

In some embodiments, the plurality of load cells determines the weight of the empty patient support apparatus. The weight of the empty patient support apparatus corresponds to the weight of non-patient items placed on the plurality of load cells on the patient support, including the currently attached removable components of the patient support apparatus.

In some embodiments, the detectors are configured to determine the presence or absence of removable components of the patient support apparatus and produce corresponding signals to the processor. The examples of the detecting mechanism include hall-effect mechanisms or switch-type mechanisms.

In some embodiments, the controller is configure to determine, in response to determining the patient support is no longer supporting the patient, the weight of the empty patient support apparatus as a function of signals received from the plurality of load cells, set and store the weight of the empty patient support apparatus as an initial tare weight of the patient support apparatus, detect, subsequent to determining the weight of the empty patient support apparatus, any subsequent removal or addition of removable components of the patient support apparatus as a function of signals received from the plurality of detectors, update the tare weight by assessing the weight of the empty patient support apparatus and the weight of currently attached removable components, and determine the weight of the patient by offsetting the tare weight.

In a sixth aspect of the preset disclosure, a method for determining and storing weights of each and every removable component on a patient support apparatus may further include the step of determining, on a controller of the patient support apparatus, whether a historical weight data of each and every removable components is stored in a memory of the patient support apparatus. The method further includes the step of detecting, on the controller, subsequent to loading each removable component on the patient support apparatus, the presence of each removable component in response to receiving a signal produced by one or more corresponding detectors. The method further includes the steps of determining an amount of weight of each and every removable component in response to receiving a signal produced by a plurality of load cells and storing the amount of weight of each and every removable component in the memory of the patient support apparatus.

In some embodiments, detecting each removable component loaded on the patient support apparatus may further include the step of loading each removable component into the corresponding mounting sockets of the patient support apparatus. Each mounting socket comprises one or more detectors that are configured to determine the presence or absence of removable components of the patient support apparatus and produce corresponding signals to the processor.

In a seventh aspect of the present disclosure, a method for adjusting a tare weight includes the steps of receiving, on a controller of a patient support apparatus, an initial tare weight of the patient support apparatus, detecting, on the controller, an addition or removal of any removable components on the patient support apparatus in response to receiving a signal produced by each of a plurality of detectors indicating a presence or absence of a corresponding removable component, determining and compensating, on the controller, an amount of weight of the removable components that has been added or removed from the patient support apparatus, and updating, on the controller, the tare weight of the patient support apparatus.

In some embodiments, compensating the amount of weight of the removable components comprises a current total amount of weight on the plurality of load cells being compensated for a first amount of weight and a second amount of weight. The first amount of weight corresponds to the weight of the removable components added to the patient support apparatus in response to signals received from the plurality of detectors, and the second amount of weight corresponds to the weight of the removable components removed from the patient support apparatus in response to signals received from the plurality of detectors.

In some embodiments, the method for adjusting a tare weight further includes receiving, on the controller of a patient support apparatus, a signal produced by each of a plurality of load cells supporting a patient support, the signal produced by each load cell indicating an amount of weight on that load cell. The method may further include the step of determining, on the controller, whether the patient support of the patient support apparatus is supporting a patient as a function of the signals produced by the plurality of load cells. The method may further include the steps of determining, on the controller, subsequent to determining that the patient support apparatus is not supporting a patient, an amount of weight of the empty patient support apparatus, and storing, on the controller, the amount of weight of the empty patient support apparatus as an initial tare weight of the patient support apparatus.

In some embodiments, determining whether the patient support is supporting a patient may further include the steps of determining a current occupancy state of the patient support apparatus. The current occupancy state of the patient support apparatus comprises at least one of an occupied state and an unoccupied state. The occupied state is indicated when the patient support is determined to be supporting the patient and the unoccupied state is indicated when the patient support is determined not to be supporting the patient.

Additional features, which alone or in combination with any other feature(s), including those listed above and those listed in the claims, may comprise patentable subject matter and will become apparent to those skilled in the art upon consideration of the following detailed description of illustrative embodiments exemplifying the best mode of carrying out the invention as presently perceived.

BRIEF DESCRIPTION OF THE DRAWINGS

The detailed description particularly refers to the accompanying figures in which:

FIG. 6 is a cross-section of a first embodiment of the mounting socket in the upper frame of the patient support apparatus of FIG. 1 with an embedded hall-effect mechanism detector;

FIG. 7 is a cross-section of a second embodiment of a mounting socket in the upper frame of the patient support apparatus of FIG. 1 with an embedded switch-type mechanism detector FIG. 7 showing a portion of a siderail in a first position;

FIG. 8 is a cross-section of the second embodiment of the mounting socket in the upper frame of the patient support apparatus of FIG. 1 with an embedded switch-type mechanism detector FIG. 7 showing the portion of the sidereal in a second position activating the switch;

DETAILED DESCRIPTION

Figure 1:
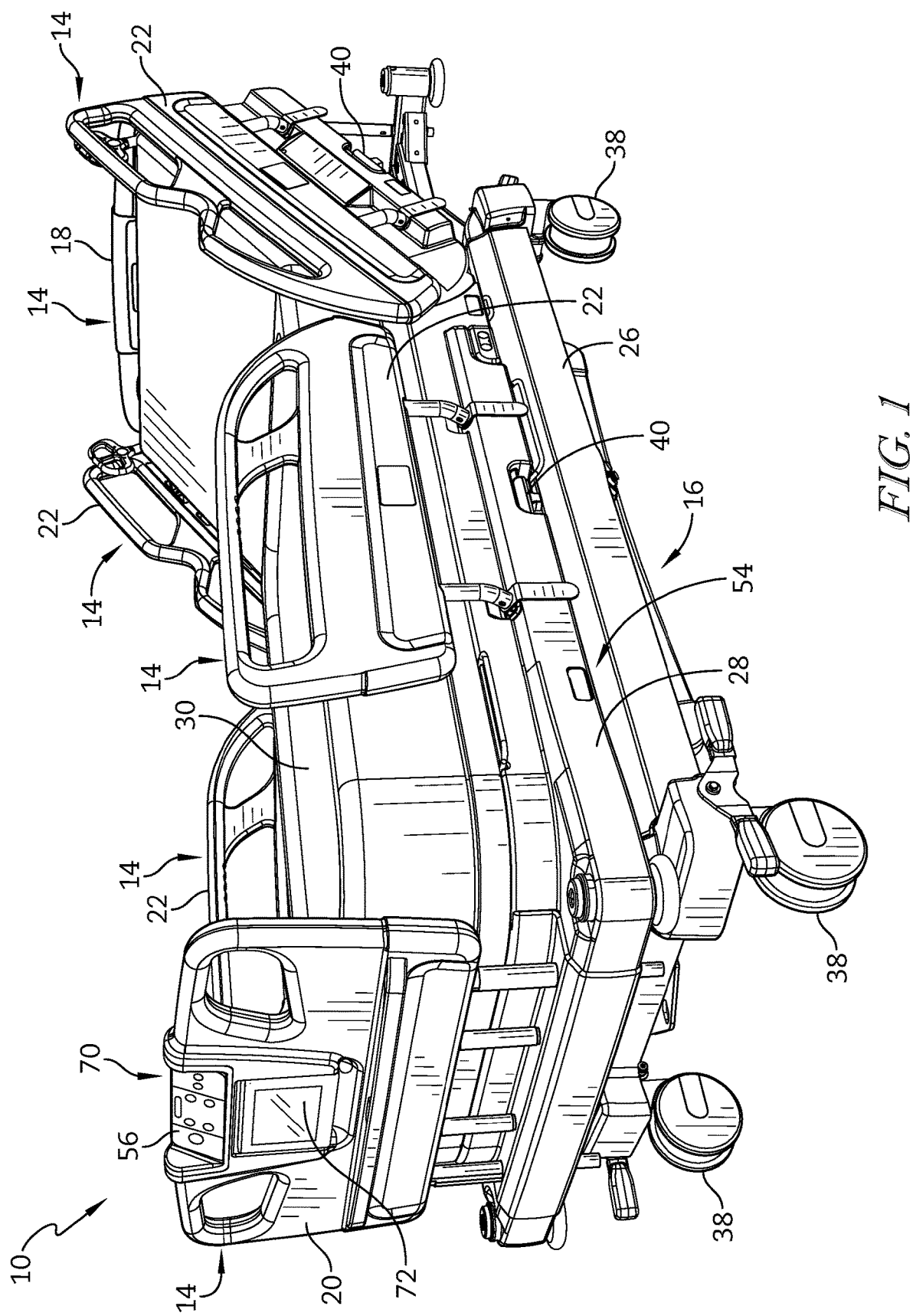
FIG. 1 is a perspective view from the foot end on the patient's left of a patient support apparatus.
Figure 4:
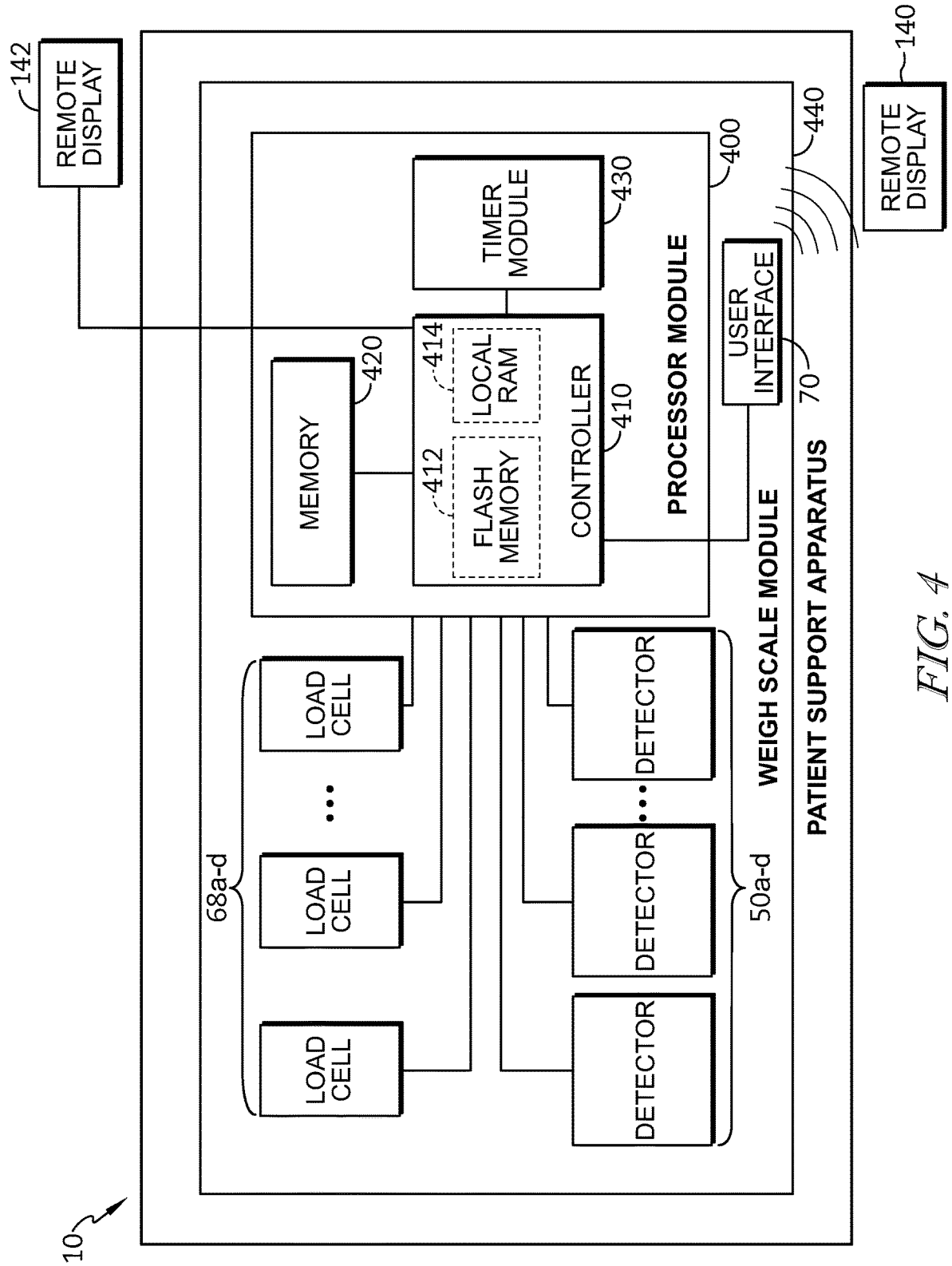
FIG. 4 is a block diagram of a portion of the electrical system of the patient support apparatus of FIG. 1 used to determine a tare weight of the patient support apparatus.

An illustrative patient support apparatus embodied as a hospital bed 10 is shown in FIG. 1. The patient support apparatus 10 of FIG. 1 has an auto-tare function, which detects and compensates for any addition or removal of one or more removable components 14 that affect determination of the true patient weight. The patient support apparatus 10 has a number of removable components 14 attached to a fixed bed frame 16 as shown in FIG. 1. The fixed bed frame 16 includes a base frame 26 with casters 38 and an upper frame 28. The upper frame 28 includes a number of mattress support sections that support a therapy surface 30. The illustrative patient support apparatus 10 has a user interface 70 that includes an input panel or control panel 56 that is affixed to the footboard 20 of the patient support apparatus 10. The user interface 70 is coupled to the controller 410 as shown in FIG. 4. In addition, the user interface 70 includes a graphical user interface 72 that includes a touchscreen panel that allows a user to modify various subsystems of the patient support apparatus 10. The graphical user interface 72 also provides graphical real-time status indications relative to the patient support apparatus 10 to the user. As will be discussed in further detail below, this real-time status provides important feedback to the user or caregiver as the operational parameters of the patient support apparatus 10 are modified.

Figure 2:
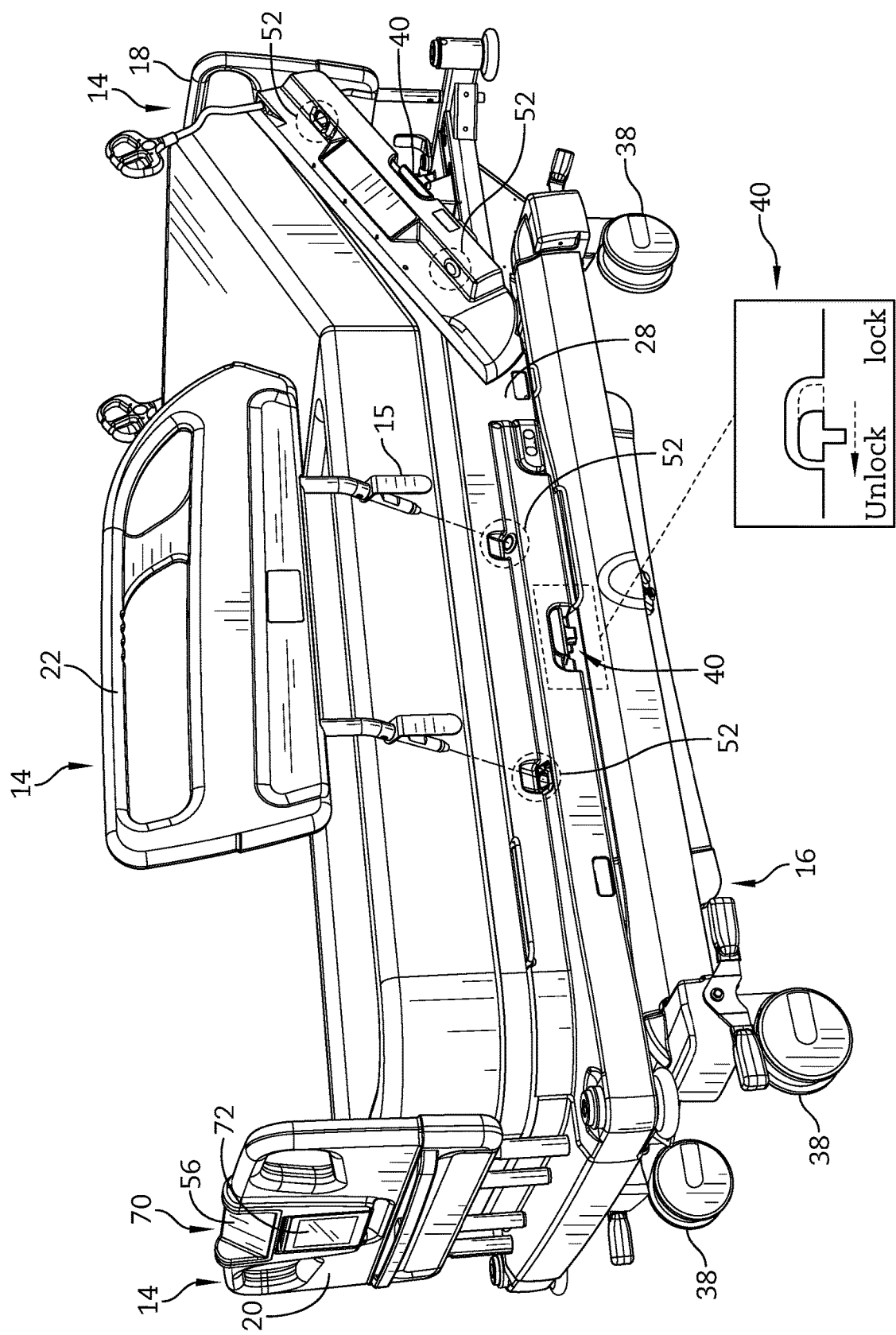
FIG. 2 is a perspective view of the patient support apparatus of FIG. 1 with a siderail detached from the patient support apparatus.
Figure 3:
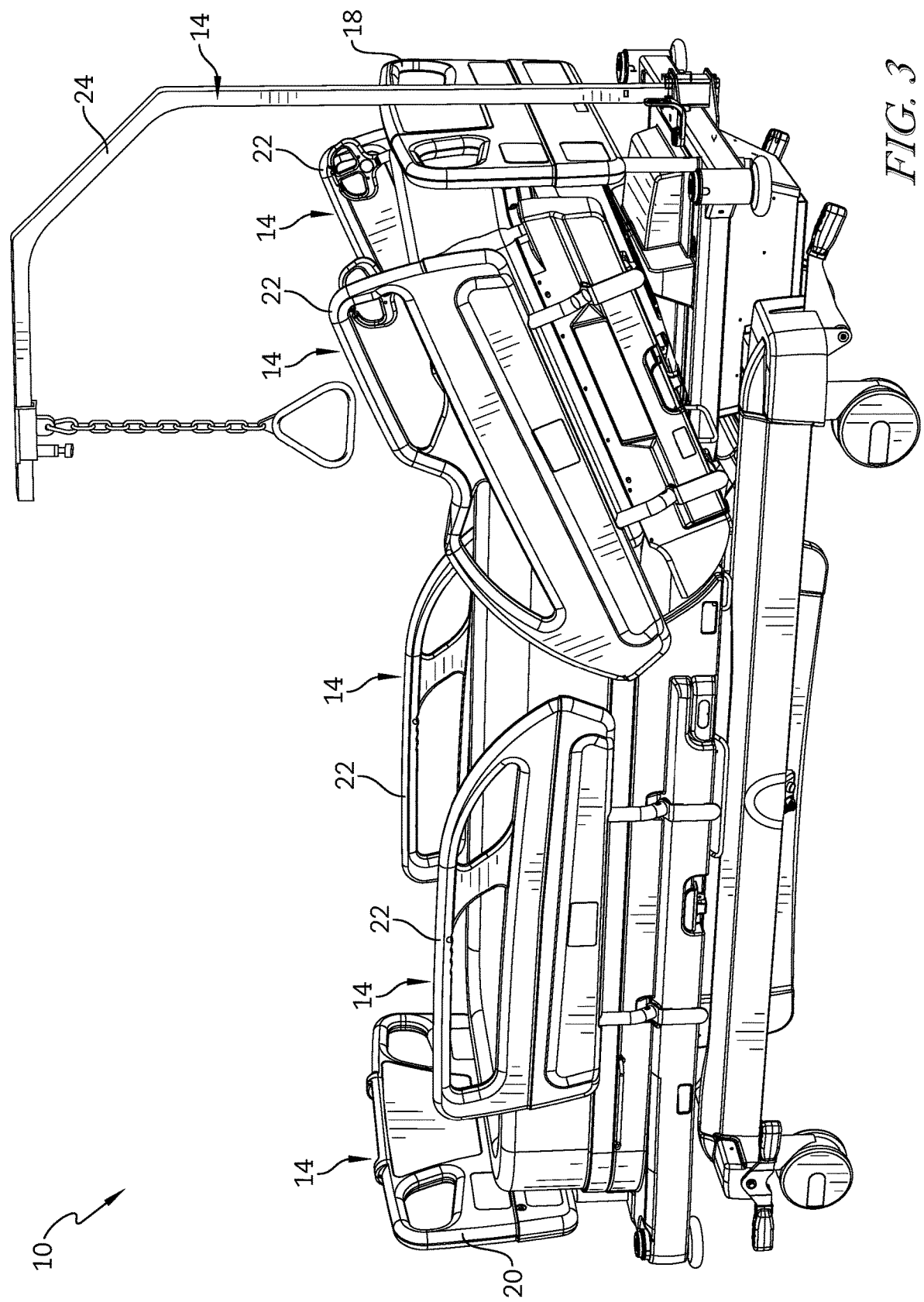
FIG. 3 is a perspective view from the head end on the patient's left of the patient support apparatus of FIG. 1, wherein the patient support apparatus further includes a patient helper attached thereto.

As shown in FIG. 3, all removable components 14, including a headboard 18, a footboard 20, siderails 22, and a patient helper 24, are in an attached position. The removable component 14 has vertically projected prongs 15 that are configured to fit into mounting sockets 52 which are located along the edges of the upper frame 28 as shown in FIG. 2. Each removable component 14 is removable from the patient support apparatus 10 to provide easier access for the patient and caregivers. For example, the siderail 22 is removed by sliding a rail latch 40 toward an unlock position and lifting up the siderail 22 from the mounting sockets 52 as shown in FIG. 2. To attach the siderail 22 back to the patient support apparatus 10, align and mount the prongs 15 of the siderail 22 into the corresponding mounting sockets 52 then slide the rail latch 40 toward a lock position.

Each mounting socket 52 has one or more detectors 50. Each detector 50 is configured to produce a signal indicative of the presence or absence of the corresponding removable component 14. Each detector 50 detects the presence of the removable component 14 by detecting the prong 15 of the removable component 14 which is vertically projected into the cylindrical space 58 of the mounting socket 52.

In some embodiments, the mounting socket 52 has one or more embedded detectors 50 mounted on the surface 60 of the cylindrical space 58 of the mounting socket 52. In an illustrative embodiment, the mounting socket 52 has the embedded hall-effect mechanism detector 50 as shown in FIG. 6. The embedded hall-effect mechanism detector 50 detects the prong 15 of the removable component 14 when the prong 15 comes in near proximity with the embedded hall-effect mechanism detector 50 in the cylindrical space 58 of the mounting socket 52. In other embodiments, the mounting socket 52 has the embedded switch-type mechanism detector 50 as shown in FIGS. 7-8. The embedded switch-type mechanism detector 50 is inactive when the corresponding removable component 14 is not attached to the patient support apparatus 10 as shown in FIG. 7. The embedded switch-type mechanism detector 50 is activated when the embedded switch 62 is in a physical contact with the tip 13 of the prong 15 of the removable component 14 as shown in FIG. 8.

Figure 11:
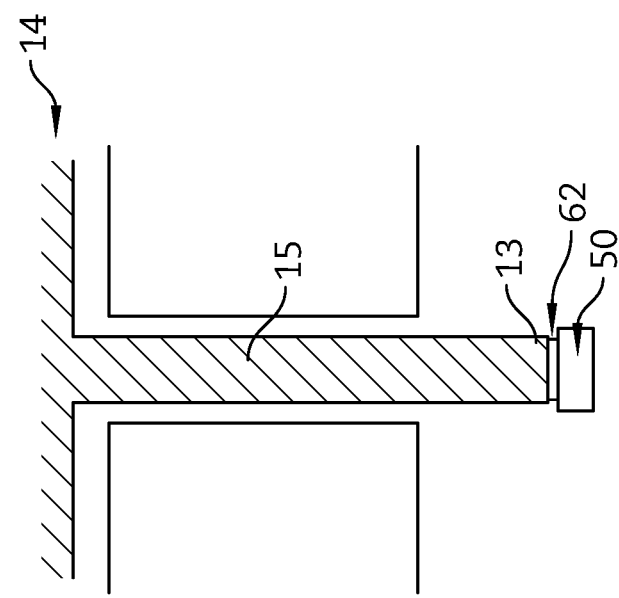
FIG. 11 is a cross-section of the fourth embodiment of the mounting socket in the upper frame of the patient support apparatus of FIG. 1 with a switch-type mechanism detector at the bottom end of the mounting socket FIG. 10 showing the portion of the sidereal in a second position activating the switch.
Figure 10:
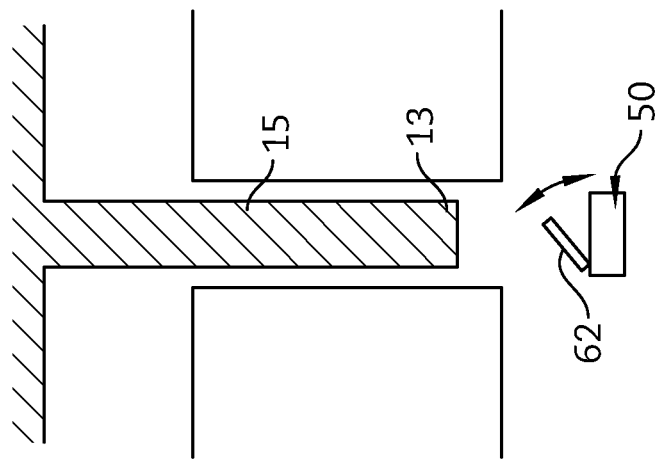
FIG. 10 is a cross-section of a fourth embodiment of a mounting socket in the upper frame of the patient support apparatus of FIG. 1 with a switch-type mechanism detector at the bottom end of the mounting socket FIG. 10 showing a portion of a siderail in a first position.
Figure 9:
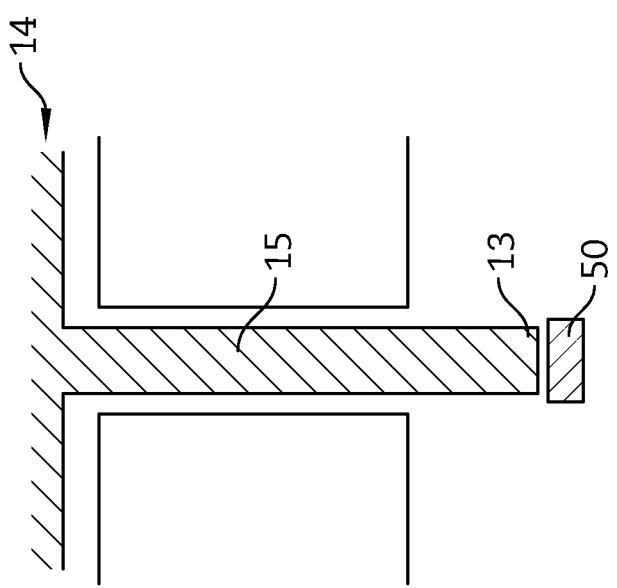
FIG. 9 is a cross-section of a third embodiment of the mounting socket in the upper frame of the patient support apparatus of FIG. 1 with a hall-effect mechanism detector positioned at the bottom end of the mounting socket.
Figure 12:
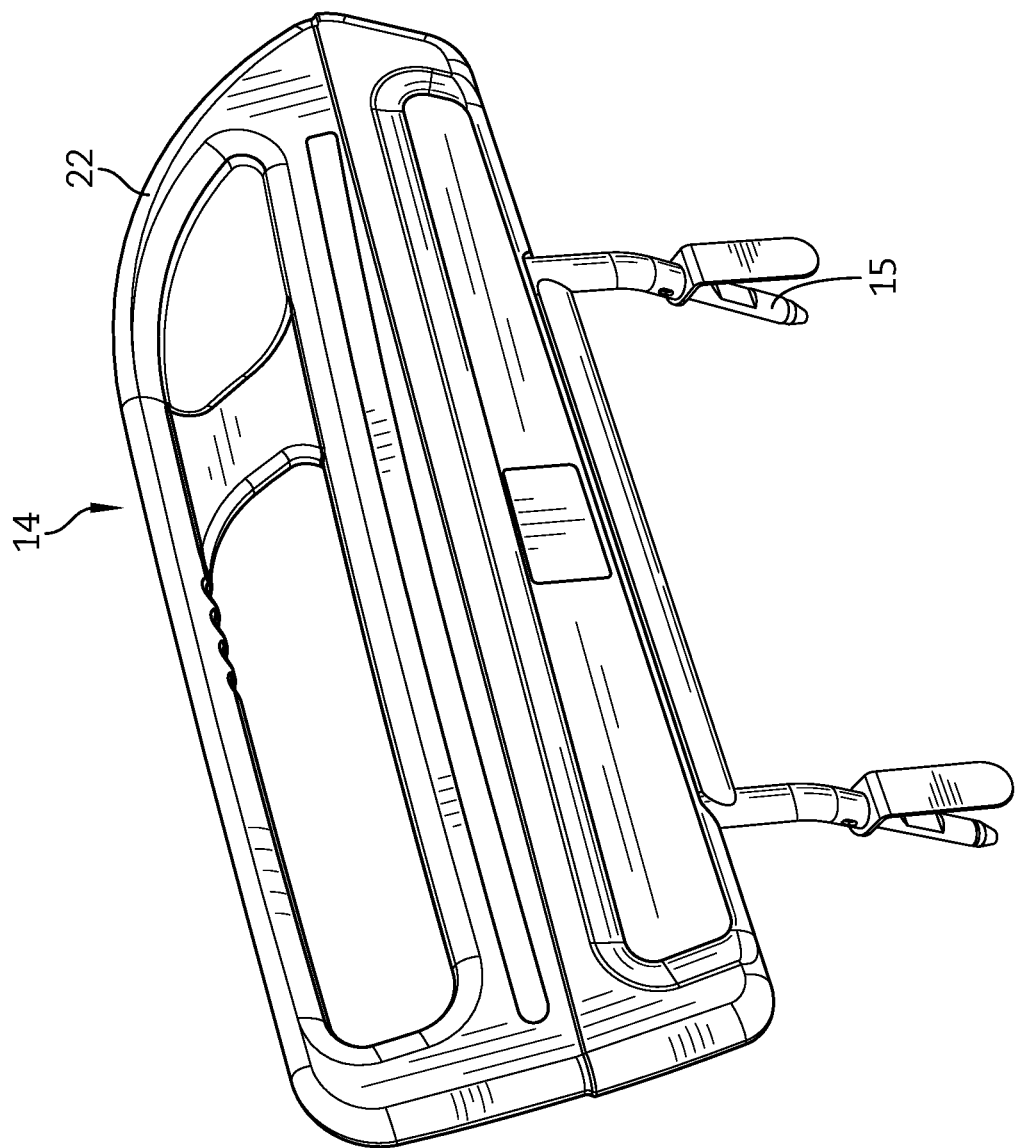
FIG. 12 is a perspective view of a siderail of the patient support apparatus of FIG. 1.

In some embodiments as shown in FIGS. 9-11, each mounting socket 52 has a detector 50 at the lower end of the cylindrical space 58 of the mounting socket 52, which is horizontally parallel to the upper frame 28. When the removable component 14 is attached to the patient support apparatus 10, the tip 13 of the prong 15 of the removable component 14 rests on the near surface of the detector 50. In an illustrative embodiment, the mounting socket 52 has the hall-effect mechanism detector 50 as shown in FIG. 9. The hall-effect mechanism detector 50 detects the tip 13 of the prong 15 of the removable component 14 when the prong 15 comes in near proximity with the detector 50 at the lower end of the cylindrical space 58 of the mounting socket 52. In other embodiments, the mounting socket 52 has the switch-type mechanism detector 50 as shown in FIGS. 10-11. The switch-type mechanism detector 50 is inactive when the corresponding removable component 14 is not attached to the patient support apparatus 10 as shown in FIG. 10. The switch-type mechanism detector 50 is activated when the switch 62 is in a physical contact with the tip 13 of the prong 15 of the removable component 14 as shown in FIG. 11.

Figure 5:
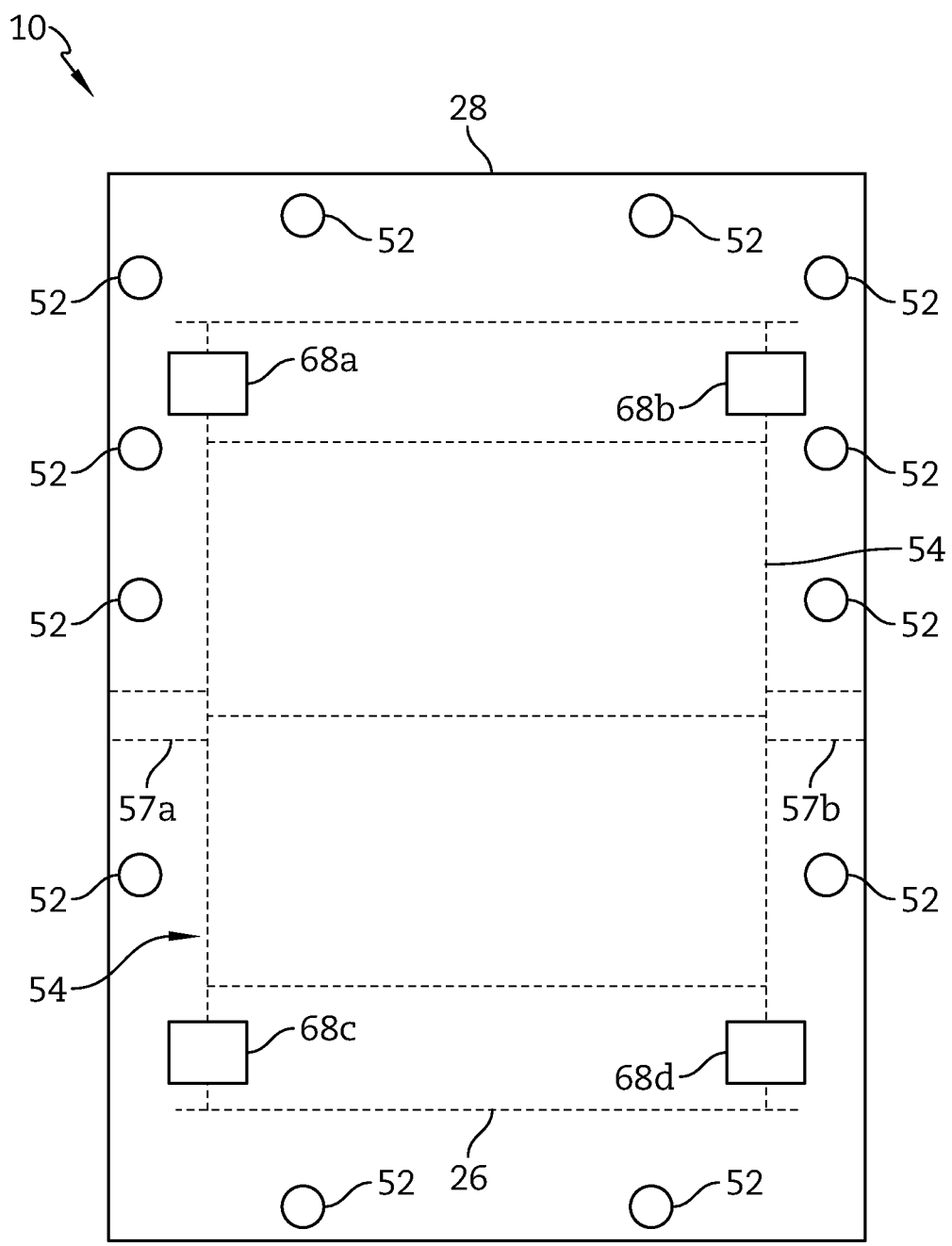
FIG. 5 is a block diagram of the positions of a number of load cells and mounting sockets relative to the patient support apparatus of FIG. 1.

Referring to FIG. 5, the base frame 26 supports a weigh frame 54 that is mounted via frame member 57a and 57b to the upper frame 28 configured to support the therapy surface 30. A number of load cells 68a-d are positioned between the weigh frame 54 and the base frame 26, wherein each load cell 68a-d is configured to produce a signal indicative of a weight supported by that load cell 68a-d from the weigh frame 54 relative to the base frame 26. In one illustrative embodiment shown diagrammatically in FIG. 4, the patient support apparatus 10 includes a weigh scale module 80 configured to automatically update a tare weight for use in determining a true patient weight. The weigh scale module 80 includes a processor module 82 that is in communication with each of the load cells 68 and detectors 50. The processor module 400 includes a microprocessor-based controller 86 having a flash memory unit 88 and a local random-access memory (RAM) unit 414. The local RAM unit 414 is utilized by the controller 86 to temporarily store information corresponding to features and functions provided by the patient support apparatus 10. More specifically, the controller 86 is configured to adjust the tare weight of the patient support apparatus 10 based on the signals provided by the load cells 68 and the detectors 50.

Figure 19:
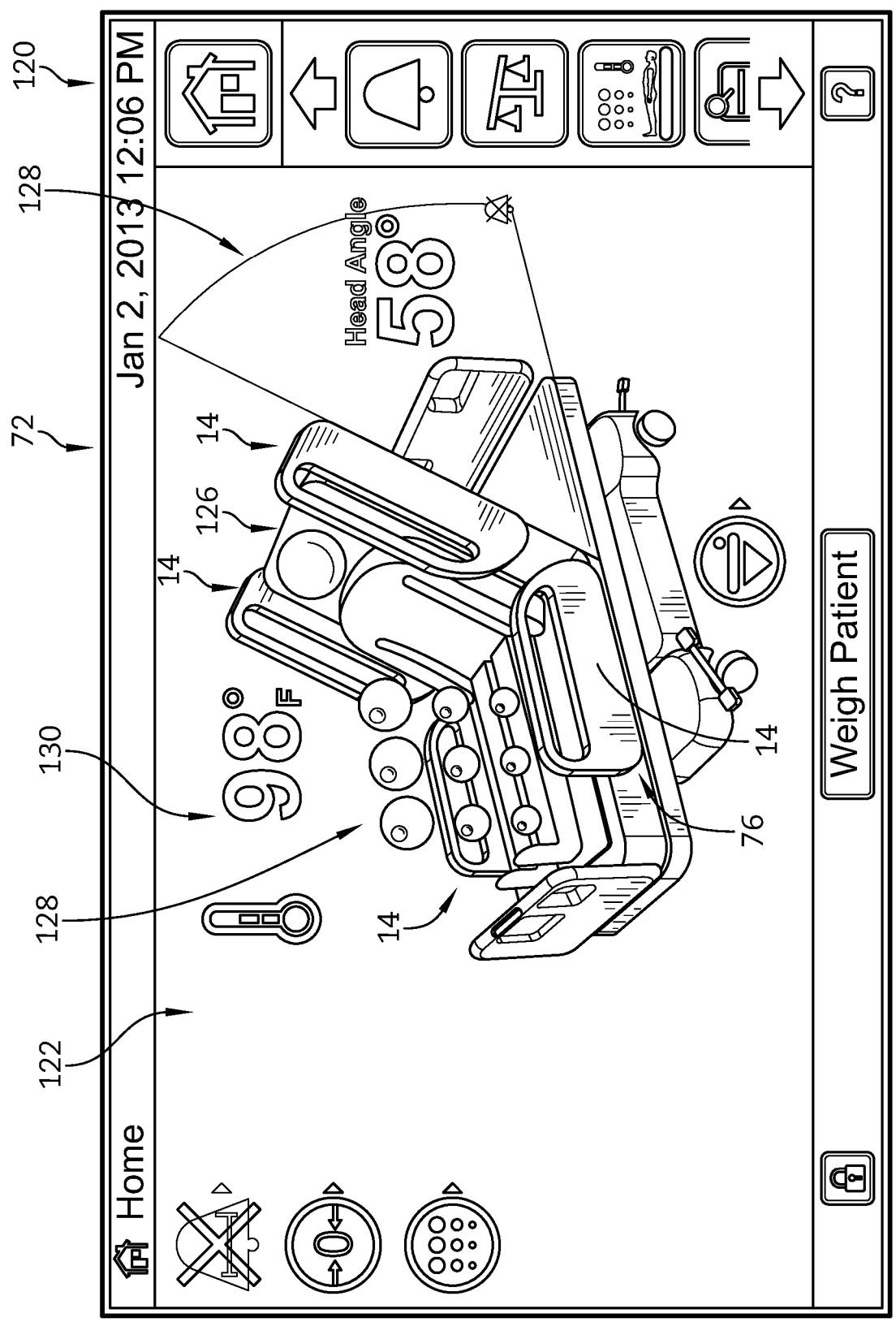
FIG. 19 is a depiction of a particular embodiment of a user interface screen of the patient support apparatus of FIG. 1, the user interface screen depicting a status of subsystems of the patient support apparatus including a depiction of the barriers present on the patient support apparatus.
Figure 20:
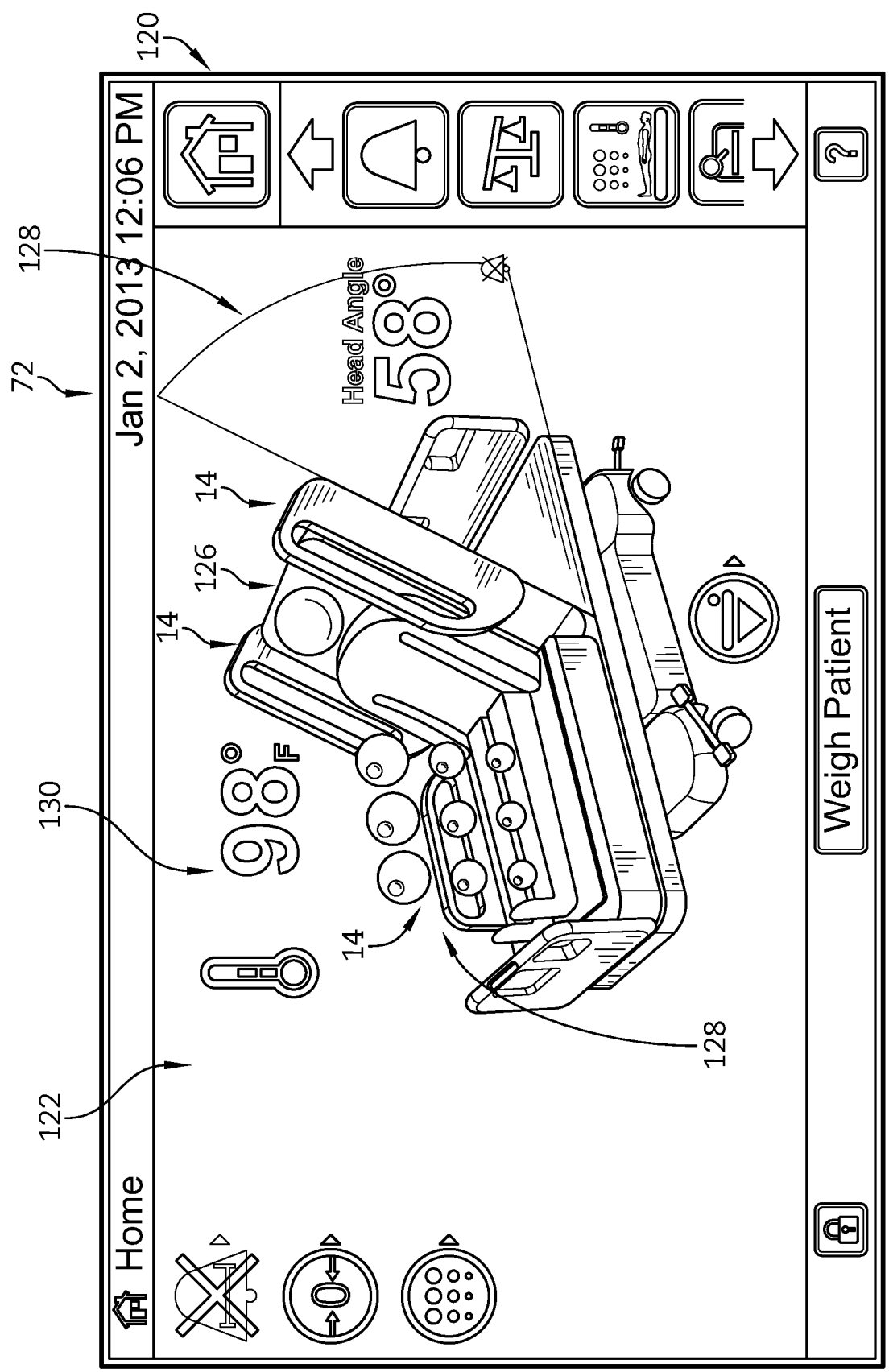
FIG. 20 is a depiction of the user interface similar to FIG. 19, with FIG. 20 showing that a siderail that has been removed from the patient support apparatus no longer appears on the user interface.

In addition, and referring to FIGS. 19 and 20, the presence or absence of the removable components 14 is indicated graphically on the touchscreen 72. The touchscreen 72 is divided into a main menu portion 120 and a status portion 122. For example, in FIG. 19, the status of several removable components 14 is indicated graphically. However, when a foot-end siderail shown in FIG. 19 and indicated by reference numeral 76 is not present, the foot-end siderail is not displayed graphically as indicated in FIG. 20. This variation provides immediate feedback to a caregiver or other user of the status of the various components of the patient support apparatus 10. In addition, a graphical representation 124 of the patient support apparatus 10 shows a head section 126 in a raised position and provides an indicia 128 of the head angle. In addition, indicia 130 in the form of animated bubbles, shows that the air fluidized portion of the surface 30 is active. The touchscreen 72 also displays the current temperature 130 through indicia on the touchscreen 72. The main menu portion 120 shows a scroll bar that has several icons that allow a user to select one of several options that may be displayed and controlled on the status portion 122.

While the disclosed embodiment shows the presence of the removable component 14, illustratively embodied as the siderail 76 as present in FIG. 19 and absent in FIG. 20, it should be understood that other approaches to indicating the absence of the siderail 76 may be used to signal the caregiver or user. For example, the missing removable component 14 may flash on and off, be shown in phantom or ghosting on the display, or may be shown on the screen but separated from the bed, as examples. Still further, the display 72 may be shown on a remote display 140 (seen in FIG. 4), such as a nurse station, for example, with the indication of the presence and absence of removable components 14 using the same techniques discussed above. A remote display may be a wired or wireless connection with the display 140 driven by display 72, or may be a duplicate display 142 that is rebuilt at a remote location by a separate controller that receives data regarding the status of the patient support apparatus 10 from controller 410 and creates the remote display from that data. Still further, the remote display 140 or 142 may be presented on a mobile computing device, such as a personal digital assistant, used by a caregiver. The presentation on the mobile computing device may in addition to both the local display 72, remote display 140 or 142, or may be an alternative to either or all.

Figure 14:
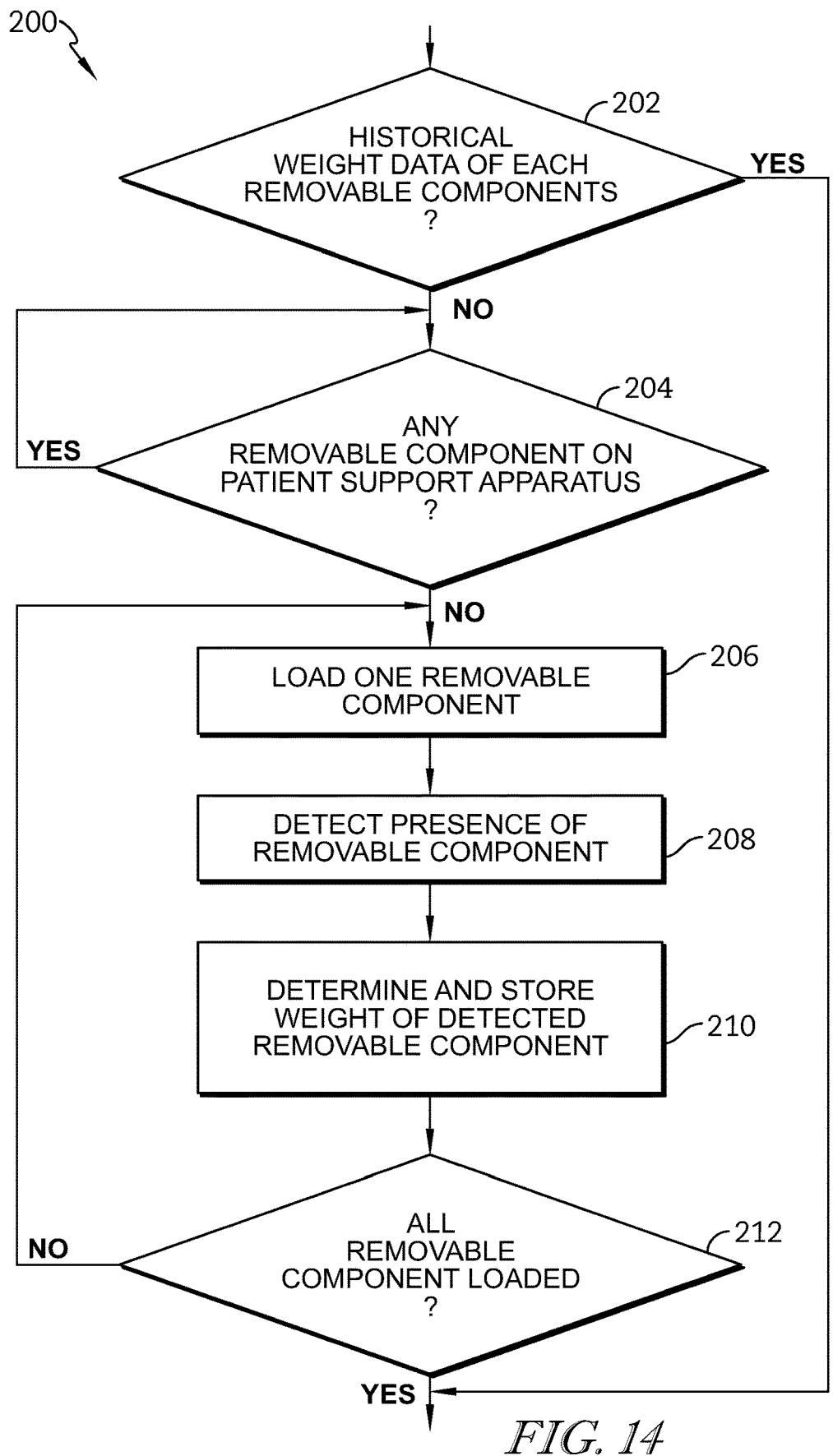
FIG. 14 is a flow chart showing a sub-routine process for determining and storing each and every removable component of the patient support apparatus that forms one part of the routine process of FIG. 13.

Referring to FIG. 14, an initial process 200 for determining the weights of each and every removable component 14 and store the weights in the memory 84 is shown. The initial process 200 illustratively begins at decision step 202 where the controller 86 is operable to determine whether historical weight data of each removable component 14 is stored in a memory 84 of the patient support apparatus 10. If the controller 86 determines that the historical weight data of each removable component 14 does not exist in the memory 84, the initial process 200 advances to decision step 204 in which the controller 86 determines whether any removable components 14 are currently attached to the patient support apparatus 10. For example, in one embodiment, the controller 86 determines whether or not any removable components 14 are currently attached to the patient support apparatus 10 in response to receiving signals produced by one or more detectors 50. If the controller 86 determines that none of the removable components 14 are currently attached to the patient support apparatus 10, the initial process 200 advances to step 206.

At step 206, one removable component 14 is added on the patient support apparatus 10 at a time. When each removable component 14 is loaded into the corresponding mounting socket 52, one or more detectors 50 detect the presence of the particular removable component 14 and produce the signal to the controller 86. When the controller 86 receives the signal from the detectors 50, the initial process 200 proceeds to step 210 where the controller 86 determines which removable component 14 is detected on the patient support apparatus 10 and stores the weight of each removable component 14 in the memory 84. Once the weights of each and every removable component 14 are stored in the memory 84, the initial process 200 proceeds to step 102 of a routine process 100.

Figure 13:
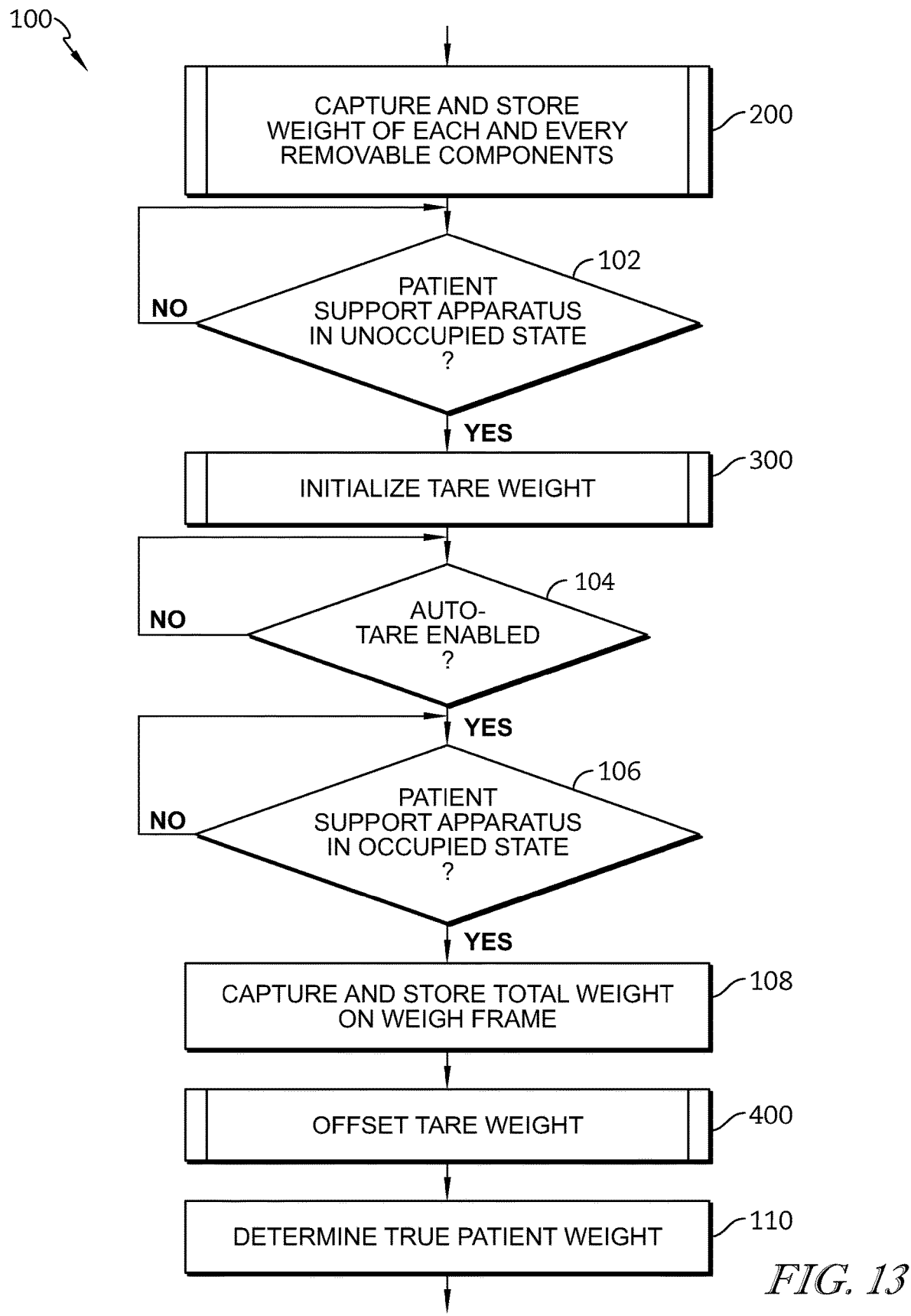
FIG. 13 is a flow chart showing a routine process performed by the processor of the patient support apparatus of FIG. 1 to determine the true patient weight.
Figure 15:
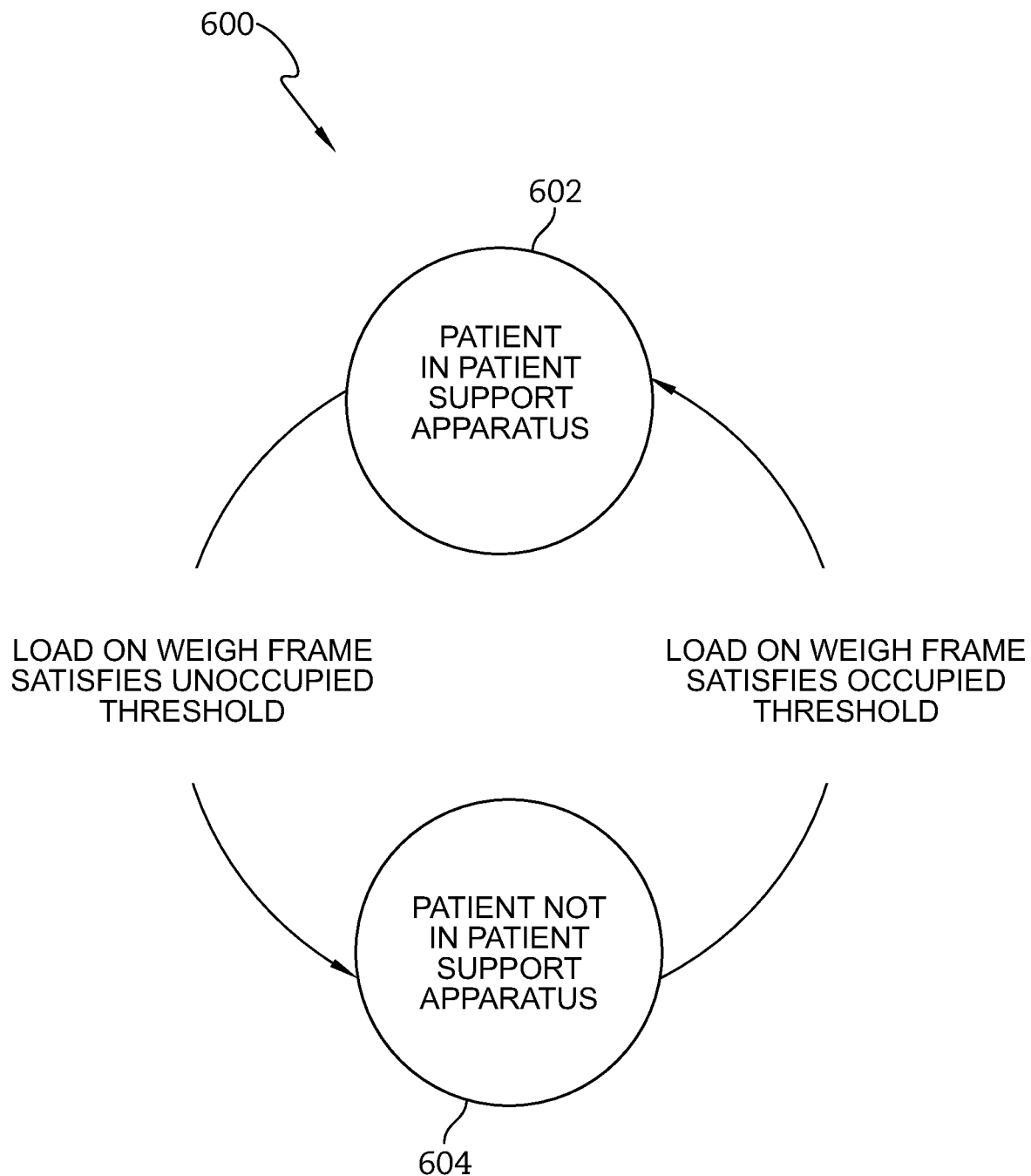
FIG. 15 is a state diagram illustrating one embodiment of a control sub-routine for determining whether a patient is being supported by the patient support apparatus that forms one part of the routine process of FIG. 13.
Figure 16:
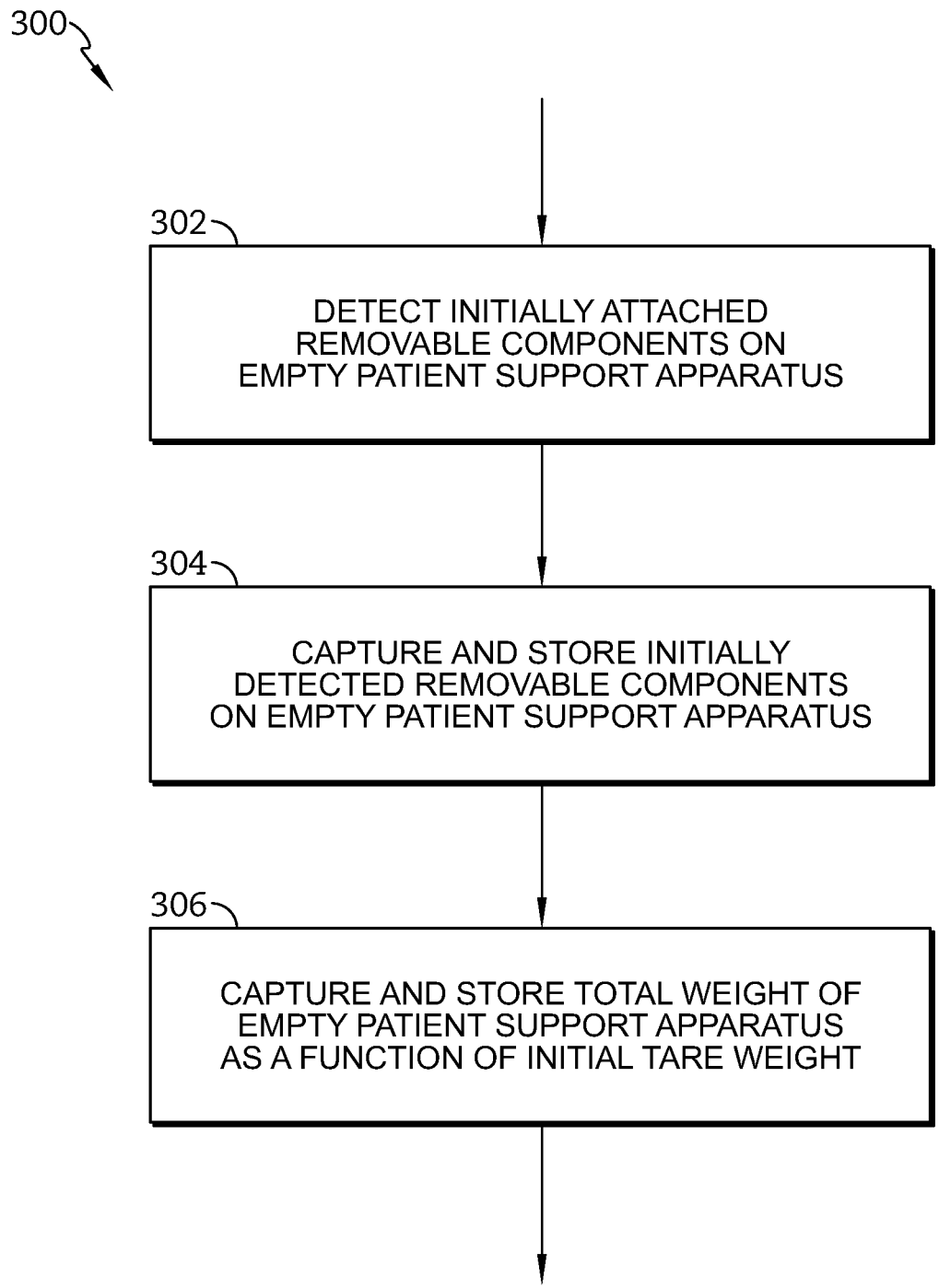
FIG. 16 is a flow chart showing a sub-routine process for initializing a tare weight that forms one part of the routine process of FIG. 13.

Referring to FIG. 13, the routine process 100 for determining the true patient weight is shown. The routine process 100 illustratively begins at decision step 102 where the controller 86 is operable to check an occupancy state of the patient support apparatus 10. FIG. 15 is a state diagram 600 illustrating one embodiment of the occupancy states of the patient support apparatus 10 as determined by the controller 86. As described above, the controller 86 determines whether or not a patient 36 is being supported by a support surface of the therapy surface 30 and updates the occupancy state accordingly. In one embodiment, the controller 86 determines two discrete states of occupancy, an occupied state 602 indicative of the patient 36 being in the patient support apparatus 10 and an unoccupied state 604 indicative of the patient 36 not being in the patient support apparatus 10. It should be understood that while the illustrative embodiment of FIG. 15 shows two discrete occupancy states, any number of occupancy states are contemplated by this disclosure. For example, the controller 86 may determine that the patient is both partially in and partially out of the patient support apparatus 10 (e.g., the patient is sitting on the edge of the patient support apparatus 10) at any given point of time.

The controller 86, in one embodiment, initializes the occupancy state of the patient support apparatus 10 to the unoccupied state 604. After initialization, the controller 86 updates the occupancy state of the patient support apparatus 10 to the occupied state 602 in response to determining that a normalized amount of weight on the weigh frame 54 satisfies a reference occupied threshold. For example, in one embodiment, the controller 86 updates the occupancy state of the patient support apparatus 10 to the occupied state 602 in response to determining that the normalized amount of weight on the weigh frame 54 meets or exceeds 31 pounds. In the illustrative embodiment, the controller 86 updates the occupancy state of the patient support apparatus 10 to the occupied state 602.

After updating the occupancy state to the occupied state 602, the controller 86 updates the occupancy state of the patient support apparatus 10 to the unoccupied state 604 in response to determining that the normalized amount of weight on the weigh frame 54 satisfies a reference unoccupied threshold. For example, in the illustrated embodiment, the controller 86 updates the occupancy state of the patient support apparatus 10 to the unoccupied state 604 in response to determining that the normalized amount of weight on the weigh frame 54 meets or falls below 65 pounds. In the present embodiment, the controller 86 updates the occupancy state of the patient support apparatus 10 to the unoccupied state 604.

Referring back to FIG. 13, if the controller 86 determines that the patient 36 is not supported on the patient support apparatus 10, the routine process 100 advances to step 300 in which the tare weight of the empty patient support apparatus 10 is initialized and stored. The initial tare weight includes the weight of the empty patient support apparatus 10 with any removable components 14 detected on the patient support apparatus 10. At step 300, the controller 86 also detects any removable components 14 initially present on the empty patient support apparatus 10 and stores the information in the local RAM unit 414. After storing the initial tare weight, the routine process 100 advances to decision step 104 where the controller 86 is operable to determine whether auto-tare functionality has been enabled on the patient support apparatus 10.

If the controller 86 determines that auto-tare functionality has been enabled on the patient support apparatus 10, the routine process 100 advances to step 106 where the controller 86 is operable to check again an occupancy state of the patient support apparatus 10 to determine whether the patient 36 is supported on the patient support apparatus 10. If the controller 86 determines that the patient 36 is now supported on the patient support apparatus 10, the routine process 100 proceeds to step 108 where the controller 86 captures and stores the total weight on a weigh frame 54 of the patient support apparatus 10. After storing the total weight of the patient support apparatus 10, the routine process 100 advances to step 400 to determine and offset the tare weight.

Figure 17:
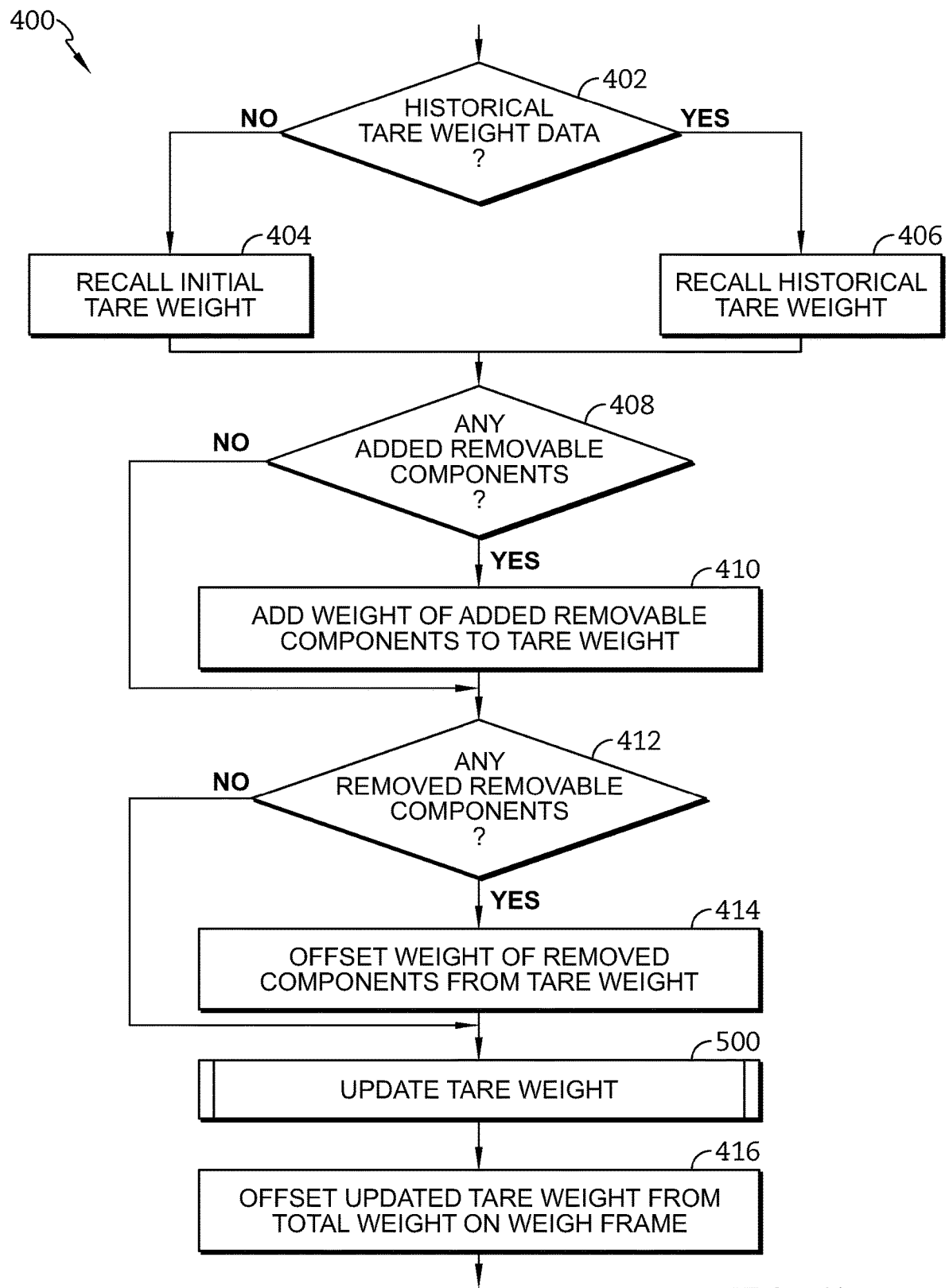
FIG. 17 is a flow chart showing a sub-routine process for determining and offsetting the tare weight that forms one part of the routine process of FIG. 13.

Referring to FIG. 17, at decision step 402, the controller 86 determines whether a historical tare weight data exists. For example, in one embodiment, the controller 86 determines whether the historical tare weight data corresponding to the patient support apparatus 10 exists. If the controller 86 determines that the historical tare weight data for the patient support apparatus 10 exists, then the routine process 100 advances to step 406 in which the controller 86 recalls the historical tare weight data. However, if the controller 86 instead determines at decision step 402 that the historical tare weight data for the patient support apparatus 10 does not exist, then the routine process 100 advances to step 404 in which the controller 86 recalls the initial tare weight data from step 300.

After determining the initial or historical tare weight in step 404 or 406, respectively, the detectors 50 detect and the controller 86 recognizes which removable components 14 was added or removed from the patient support apparatus 10. If the detectors 50 detect any removable components 14 added on the patient support apparatus 10 at decision step 408, the controller 86 adds the predetermined weights of the added removable components 14 to the initial or historical tare weight. If, however, the detectors 50 detect any removable components 14 removed from the patient support apparatus 10 at decision step 412, the controller 86 subtracts the predetermined weights of the removed removable components 14 from the initial or historical tare weight. Accordingly, at step 500, the controller 86 updates the initial or historical tare weight as a function of the historical tare weight data.

Figure 18:
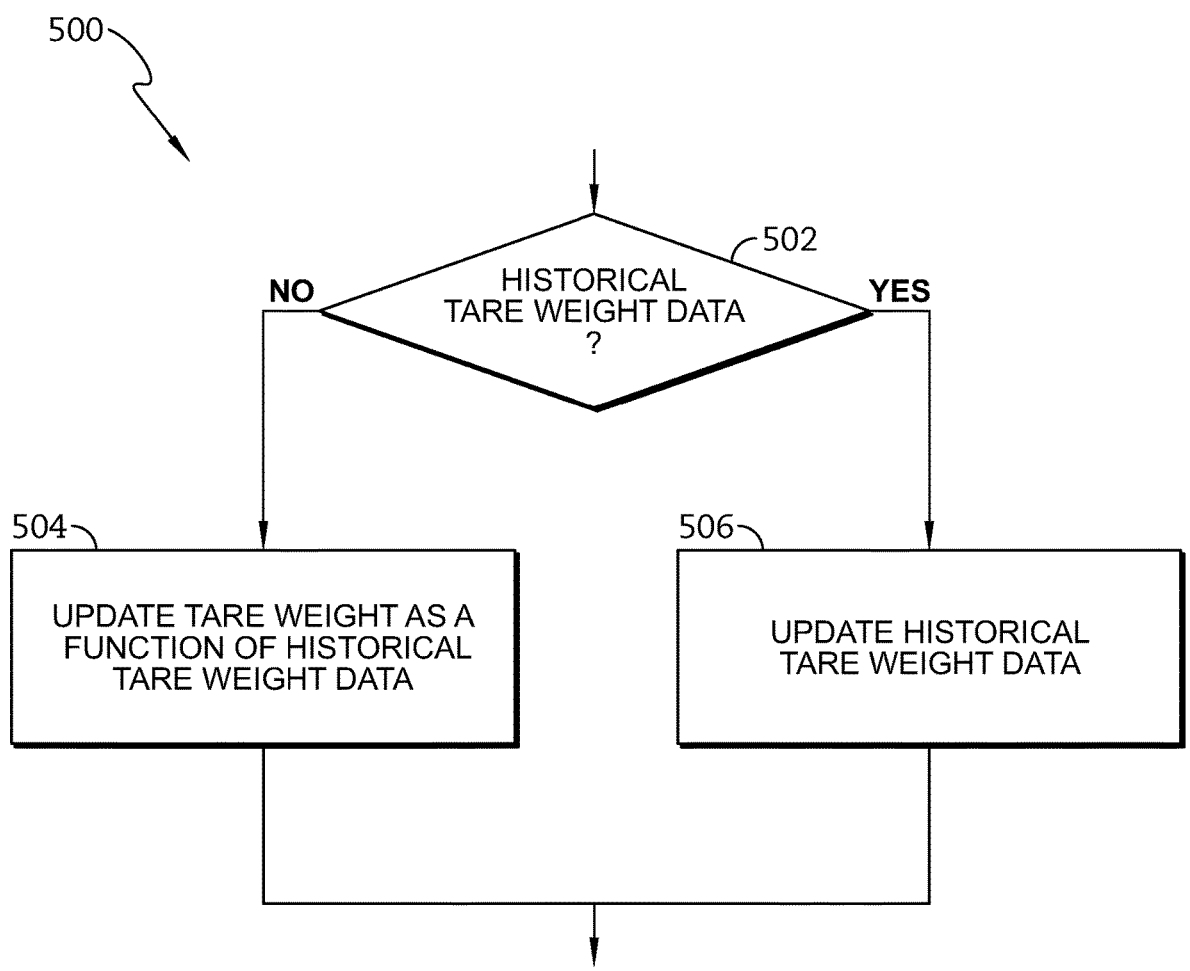
FIG. 18 is a flow chart showing a sub-routine process for updating a tare weight as a function of historical weight information that forms one part of the routine of FIG. 17.

Referring to FIG. 18, at decision step 502, the controller 86 determines whether a historical tare weight data exists. For example, in one embodiment, the controller 86 determines whether the historical tare weight data corresponding to the patient support apparatus 10 exists. If the controller 86 determines that the historical tare weight data for the patient support apparatus 10 exists, then the process 100 advances to step 506 in which the controller 86 update the existing historical tare weight data. However, if the controller 86 instead determines at decision step 502 that the historical tare weight data for the patient support apparatus 10 does not exist, then the process 500 advances to step 504 in which the controller 86 update the new tare weight as a function of historical tare weight data.

After updating and storing the tare weight of the current patient support apparatus 10 at step 500, the routine process 100 proceeds to step 110 to determine the true patient weight. At step 110, the controller 86 determines the true weight of patient that is solely attributable to the patient by offsetting the updated tare weight from the total amount of weight on the patient support apparatus 10.

Although certain illustrative embodiments have been described in detail above, variations and modifications exist within the scope and spirit of this disclosure as described and as defined in the following claims.

The invention claimed is:

1. A patient support apparatus comprising
a plurality of load cells configured to produce a signal indicative of an amount of weight on that load cell,
a detector configured to produce a signal indicative of a presence of a removable component, and
a controller in communication with the plurality of the load cells and the of detector, the controller configured to:
receive the signal produced by each of the load cells and the detector, and
determine a weight of the patient being supported on the patient support apparatus,
detect, subsequent to determining the weight of the patient, any subsequent removal or addition of the removable component the patient support apparatus based on the signal produced by the detector, and
update the weight of the patient being supported on the patient support apparatus considering the effect of the removal or addition of the removable component.

2. The patient support apparatus of claim 1, wherein the controller is further configured to: determine an initial tare weight of the empty patient support apparatus, and determine whether the patient support apparatus is supporting a patient as a function of the signals produced by the plurality of load cells.

3. The patient support apparatus of claim 2, wherein to determine whether the patient support apparatus is supporting the patient comprises determining a current occupancy state of the patient support apparatus, wherein the current occupancy state of the patient support apparatus comprises at least one of an occupied state and an unoccupied state, the occupied state being indicated when the patient support apparatus is determined to be supporting the patient and the unoccupied state being indicated when the patient support apparatus is determined not to be supporting the patient.

4. The patient support apparatus of claim 2, wherein the controller is further configured to: automatically update the tare weight of the patient support apparatus.

5. The patient support apparatus of claim 2, wherein the tare weight of the patient support apparatus comprises a total amount of weight of the empty patient support apparatus being compensated for a first amount of weight and second amount of weight, the first amount of weight corresponding to the weight of the subsequently added removable component, and the second amount of weight corresponding to the weight of the subsequently removed removable component of the patient support apparatus.

6. The patient support apparatus of claim 5, wherein updating the tare weight in response to detecting the addition or removal of the removable component comprises updating the tare weight in response to (i) determining that the patient support apparatus is no longer supporting the patient, (ii) storing the removable component initially detected on the empty patient support apparatus, (iii) storing total weight of the empty patient support apparatus as a function of initial tare weight, and (iv) updating the tare weight by supplementing the weight of the removable component added to the patient support apparatus or by offsetting the weight of the removable component removed from the patient support apparatus in response to signals received from the detector.

7. The patient support apparatus of claim 2, wherein updating a weight of the patient includes (i) determining the weight of the empty patient support apparatus as a function of signals received from the plurality of load cells, (ii) determining the presence or absence of removable component of the patient support apparatus in response to the signals received from the detector, (iii) determining the tare weight of the patient support apparatus, and (iv) offsetting the updated tare weight from the total amount of weight of the patient support apparatus.

8. The patient support apparatus of claim 1, wherein the controller is further configured to:
  determine a normalized amount of weight of the removable component of the patient support apparatus as a function of the signals produced by the plurality of load cells,
  detect the removable component currently attached to the patient support apparatus in response to detecting a presence or absence of the removable component by the detector,
  determine and store a total weight of the removable component currently attached to the patient support apparatus, and
  detect any subsequent addition or removal of the removable component from the patient support apparatus.

9. The patient support apparatus of claim 1, wherein the controller is further configured to:
  set an initial occupancy state of the patient support apparatus to an unoccupied state,
  determine a normalized amount of weight on the plurality of load cells as a function of the signals produced by the plurality of load cells,
  set the current occupancy state of the patient support apparatus to the occupied state in response to the normalized amount of weight on the plurality of load cells satisfying an occupied condition, the occupied condition defining a first normalized threshold value for which the normalized amount of weight on the plurality of load cells must exceed, and
  set the current occupancy state of the patient support apparatus to the unoccupied state in response to the normalized amount of weight on the plurality of load cells satisfying an unoccupied condition, the unoccupied condition defining a second normalized threshold value for which the normalized amount of weight on the plurality of load cells must be below.

10. The patient support apparatus of claim 9, wherein the controller is further configured to determine, in response to determining that the patient support apparatus is no longer supporting the patient, a total amount of weight of the empty patient support apparatus as a function of signals received from the plurality of load cells, and set and store the total amount of weight of the empty patient support apparatus as an initial tare weight of the patient support apparatus.

11. The patient support apparatus of claim 10, wherein the total amount of weight of the empty patient support apparatus comprises the amount of weight on the plurality of load cells of the empty patient support apparatus, wherein the amount of weight of the empty patient support apparatus includes a weight of the removable component currently attached to the empty patient support apparatus.

12. The patient support apparatus of claim 1, wherein the controller comprises a processor; and at least one machine-readable storage medium comprising a plurality of instructions, that in response to being executed by the processor, automatically determine the patient weight based on the signals from the load cells and the sensors.

13. The patient support apparatus of claim 12, wherein determining the presence or absence of removable component of the patient support apparatus comprises detecting the signal produced by the detector associated with the removable component.

14. The patient support apparatus of claim 13, wherein the removable component of the patient support apparatus includes headboard, footboard, siderail, infusion support, drainage container, or urinal container.

15. The patient support apparatus of claim 14, wherein the patient support apparatus further comprises a user interface that includes a graphical display and the presence or absence of the removable component is indicated by an icon representation of the patient support apparatus.

16. The patient support apparatus of claim 15, wherein the information regarding the presence or absence of the removable component is transmitted to a graphical display remote from the patient support apparatus.

17. The patient support apparatus of claim 16, wherein the remote graphical display is a mobile computing device associated with a particular caregiver.

18. A method of determining the weight of a removable component of a patient support apparatus that includes a plurality of load cells, the method comprising
  determining an initial tare weight for the patient support apparatus,
  prompting a user to add a removable component to the patient support apparatus,
  detecting the presence of the removable component by a sensor associated with the removable component,
  determining, using the load cells, the weight of the removable component.

19. The method of claim 18, further comprising storing the weight of the removable component in a memory device, determining an updated tare weight based on the added weight of the removable component, and storing the updated tare weight in a memory device.

20. The method of claim 18, further comprising monitoring the sensor associated with the removable component and the sensor associated with the second removable component to determine if the removable component is removed, and, if a removable component is detected to be removed, updating the tare weight to account for the removal of the weight of the component that has been removed.

* * * * *